US006686462B2

(12) United States Patent
Rosowsky et al.

(10) Patent No.: US 6,686,462 B2
(45) Date of Patent: *Feb. 3, 2004

(54) ANTIVIRAL COMPOUNDS AND METHODS OF ADMINISTRATION

(75) Inventors: Andre Rosowsky, Needham, MA (US); Karl Y. Hostetler, Del Mar, CA (US); James R. Beadle, San Diego, CA (US); Ganesh D. Kini, San Diego, CA (US); Douglas D. Richman, La Jolla, CA (US)

(73) Assignees: The Regents of the University of California, Oakland, CA (US); Dana-Farber Cancer Institute, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/808,847

(22) Filed: Feb. 28, 1997

(65) Prior Publication Data

US 2002/0082247 A1 Jun. 27, 2002

(51) Int. Cl.$^7$ .......................... A61K 31/70; C07H 19/10
(52) U.S. Cl. ...................... 536/26.8; 536/26.8
(58) Field of Search ................ 514/47, 48, 51; 536/26.5, 26.7, 26.71, 26.72, 26.74, 26.8

(56) References Cited

U.S. PATENT DOCUMENTS

| | | | | |
|---|---|---|---|---|
| 4,056,673 A | * | 11/1977 | Heimer et al. | 536/26.3 |
| 5,132,414 A | * | 7/1992 | Rosowsky et al. | 536/26.7 |
| 5,194,654 A | * | 3/1993 | Hostetler et al. | 558/152 |
| 5,223,263 A | * | 6/1993 | Hostetler et al. | 424/450 |
| 5,359,115 A | * | 10/1994 | Campbell et al. | 558/110 |
| 5,411,947 A | * | 5/1995 | Hostetler et al. | 514/43 |
| 5,463,092 A | * | 10/1995 | Hostetler et al. | 554/40 |
| 5,521,161 A | * | 5/1996 | Malley et al. | 514/45 |

FOREIGN PATENT DOCUMENTS

| | | | |
|---|---|---|---|
| EP | 0508687 | * | 10/1992 |
| WO | 9210991 | | 7/1992 |
| WO | 9418216 | * | 8/1994 |
| WO | 9427590 | * | 12/1994 |
| WO | 9615132 | | 5/1996 |
| WO | WO 98/39831 | | 12/1996 |

OTHER PUBLICATIONS

Saha et al., "Phosphonoformate Esters of Anti–HIV Nucleosides: 3'–Azido–3'–deoxythymidine and 2',3'–Dideoxycytidine Derivatives Containing a Small 5'–(O–Alkoxycarbonylphosphinyl) or 5'–(O–Cholesterylcarbonylphosphinyl) Substituent," *Nucleosides Nucleotides*, 10(7), 1465–1475 (1991); *Chem. Abstr.*, 116(7), p. 912, Abstr. No. 59865c (Feb. 17, 1992).*

Rosowsky et al. (II), "Synthesis and In Vitro Activity of Long–Chain 5'–O –[(Alkoxy)phosphinyl] –3'–azido–3'–deoxythymidines Against Wild–Type and AZT– and Foscarnet–Resistant Strains of HIV–1," *Journal of Medicinal Chemistry*, 40(16), 2482–2690 (Aug. 1, 1997).*

Vila et al., "Absence of Viral Rebound After Treatment of HIV–Infected Patients with Didanosine [ddI] and Hydroxycarbamide [Hydroxyurea]," *Lancet*, 350(9078), 635–636 (Aug. 30, 1997).*

Hostetler et al. (V), "Synthesis and Antiretroviral Activity of Phospholipid Analogs of Azidothymidine and Other Antiviral Nucleosides," *Journal of Biological Chemistry*, 265(11), 6112–6117 (Apr. 15, 1990).*

Hostetler et al. (VI), "Phosphatidylazidothymidine— Mechanism of Antiretroviral Action in CEM Cells," *Journal of Biological Chemistry*, 266(18), 11714–11717 (Jun. 25, 1991).*

Lambert et al., "Synthesis and Antiviral Activity of Phosphonoacetic Acid and Phosphonoformic Acid Esters of 5–Bromo–2'–deoxyuridine and Related Pyrimidine Nucleosides and Acyclonucleosides," *Journal of Medicinal Chemistry*, 32(2), 367–374 (Feb., 1989).*

Tisdale et al., "Combination of Mutations in Human Immunodeficiency Virus Type 1 Reverse Transcriptase Required for Resistance to the Carbocyclic Nucleoside 1592U89," *Antimicrobial Agents and Chemotherapy*, 41(5), 1094–1098 (May, 1997), Copy supplied by applicant.*

Moraleda et al., "Lack of Effect of Antiviral Therapy in Nondividing Hepatocyte Cultures on the Closed Circular DNA of Woodchuck Hepatitis Virus," *Journal of Virology*, 71(12), 9392–9399 (Dec., 1997), Copy supplied by applicant.*

Rajagopalan et al., "High Performance Liquid Chromatographic Determination of (−)–α–D–2,6–Diaminopurine Dioxolane and Its Metabolite, Dioxolane Guanosine, Using Ultraviolet and On–Line Radiochemical Detection," *Journal of Chromatography B*, 672(1), 119–124 (Oct. 6, 1995), Copy supplied by applicant.*

Balzarini et al., "Marked Inhibitory Activity of Masked Aryloxy Aminoacyl Phosphoamidate Derivatives of Dideoxynucleoside Analogues Against VISNA Virus Infection," *Journal of Acquired Immune Deficiency Syndrome in Human Retrovirology*, 17(4), 296–302 (Apr. 1, 1998); only abstract supplied, Copy supplied by applicant.*

(List continued on next page.)

*Primary Examiner*—James O. Wilson
*Assistant Examiner*—L. Eric Crane
(74) *Attorney, Agent, or Firm*—Peter F. Corless; Edwards & Angell, LLP

(57) ABSTRACT

The invention provides lipophilic phosphonoacid/nucleoside conjugates that exhibit exceptional antiviral activity, including activity against drug-resistant HIV strains. Compounds of the invention include phosphonoacid/nucleoside conjugates where the carboxyl group and phosphonyl groups of the phosphonacid are esterified whereby the compound contains at least one lipophilic group and at least one nucleoside group.

10 Claims, No Drawings

OTHER PUBLICATIONS

Yajima et al., "Direct Transport of 2',3'-Didehydro-3'-deoxythymidine (D4T) and ITs Ester Derivatives to the Cerebrospinal Fluid Via the Nasal Mucous Membrane in Rats," *Biol. Pharm. Bull., 21*(3), 272–277 (Mar., 1998); only abstract supplied, Copy supplied by applicant.*

J. Noren et al., *J. Med. Chem.*, 26:264–270 (1983). (issue No. 2), Month of publication data is unavailable.

L. Phillips et al., *Tetrahedron Letters*, 30:7141–7144 (1989).(issue No. 51), Month of publication data is unavailable.

R. Iyer et al., *J. Pharm. Sci.*, 83:1269–1273 (1994). (Issue No. 9, Sep. 1994).

M. Vaghefi et al., *J. Med. Chem.*, 29:1389–1393 (1986). (Issue No. 8), Month of publicationa data is unavailable.

A. Rosowsky et al., *Biochem. Biophys. Res. Commun.*, 172:288–294 (1990).(Oct. 15, 1990).

K. Hostetler et al., *Antiviral Research*, 3159–67 (1996), Month of publication data is unavailable.

A. Charvet et al., *J. Med. Chem.*, 37:2216–2223 (1994). (Issue No. 14), Month of publication data is unavailable.

Griengl et al., *J. Med. Chem.*, 31:1831–1839 (1988). (Issue No. 9), Month of publication data is unavailable.

A. Charvet et al., *Antiviral Research*, 25:161–168 (1994), Month of publication data is unavailable.

R. Lambert et al., *J. Med. Chem.*, 32:367–374 (1989). (Issue No. 2), Month of publication data is unavailable.

C. Neto et al., *Biochem. Biophys. Res. Commun.*, 171(1):458–464 (1990).(Aug. 31, 1990).

H. Bazin et al., *Biochem. Biophys. Res. Commun.*, 38(1):109–119 (1989), Month of publication data is unavailable.

B. Eriksson et al., *Antimicr. Agents and Chemoth.*, 33(5):663–669 (1989). (May, 1989).

Tisdale et al., "Combination of Mutations in Human Immunodeficiency Virus Type 1 Reverse Transcriptase Required for Resistance to the Carbocyclic Nucleoside 1592U89," *Antimicrobial Agents and Chemotherapy, 41*(5), 1094–1098 (May 1997).

Moraleda et al., "Lack of Effect of Antiviral Therapy in Nondividing Hepatocyte Cultures on the Closed Circular DNA of Woodchuck Hepatitis Virus," *J. Virology, 71*(12), 9392–9399 (Dec. 1997).

Rajagopalan et al., "High Performance Liquid Chromatographic Determination of (–)-α-D-2,6-Diaminopurine Dioxolane and Its Metabolite, Dioxolane Guanosine, Using Ultraviolet and On-Line Radiochemical Detection," *J. Chromatography B, 672*(1), 119–124 (Oct. 6, 1995).

Balzarini et al., "Marked Inhibitory Activity of Masked Aryloxy Aminoacyl Phosphoamidate Derivatives of Dideoxynucleoside Analogues Against VISNA Virus Infection," *J. Acquired Immune Defic. Syndr. Hum. Retrovirology, 17*(4), 296–302 (Apr. 1, 1998); only abstract supplied.

Yajima et al., "Direct Transport of 2',3'-Didehydro-3'-deoxythymidine (D4T) and ITs Ester Derivatives to the Cerebrospinal Fluid Via the Nasal Mucous Membrane in Rats," *Biol. Pharm. Bull., 21*(3), 272–277 (Mar. 1998); only abstract supplied.

* cited by examiner

ANTIVIRAL COMPOUNDS AND METHODS OF ADMINISTRATION

BACKGROUND OF THE INVENTION

1. Field of the Invention

The present invention relates to novel nucleoside and phosphonoacid lipophilic conjugates and methods of treatment such as treatment of virally infected cells by administering one or more of the conjugates of the invention. Compounds of the invention include phosphonoacid/nucleoside conjugates where the carboxyl group and phosphonyl groups of the phosphonoacid are esterified whereby the compound contains at least one lipophilic group and at least one nucleoside group.

2. Background

The human immunodeficiency virus type 1 (HIV-1, also referred to as HTLV-III, LAV or HTLV-III/LAV) and, to a lesser extent, human immunodeficiency virus type 2 (HIV-2) is the etiological agent of the acquired immune deficiency syndrome (AIDS) and related disorders. See, for example, Barre-Sinoussi et al., *Science*, 220:868–871 (1983); Gallo et al., *Science*, 224:500–503 (1984).

Methods for treating individuals infected by HIV have focussed on preventing integration of the virus into the host cell's chromosome or on stages other than provirus. Thus one area of interest has been drugs that affect reverse transcriptase of HIV.

A number of dideoxy nucleosides have shown activity as reverse transcriptase inhibitors. In particular, AZT (zidovudine, 3'-azido-3'-deoxythymidine), ddI (2',3'-dideoxyinosine), ddC (2',3'-dideoxycytidine), d4T (2',3'-dideoxy-2',3'-dihydro-thymidine), (−) 2',3'-dideoxy-3'-thiacytosine (3TC), (−) 2',3'-dideoxy-5-fluoro-3'-thiacytosine (FTC) and 1592U89 (Glaxo-Wellcome) have been used clinically for treatment of HIV infections.

Foscarnet, the trisodium salt of phosphonoformic acid (PFA, $HOOCP(=O)(OH)_2$) is also a potent inhibitor of reverse transcriptase from human immunodeficiency virus type 1 (HIV-1). PFA inhibits replication of the virus in vitro and has been used clinically against AIDS. See E. Helgstrand et al., *Science*, 201:819–821 (1978); B. Oberg, *Pharmacol. Ther.*, 40:213–285 (1989); H. Sundquist et al., *J. Gen. Virol.*, 45:273–281 (1979); L. Vrang et al., *Antimicrob. Agents Chemother.*, 29:8967–872 (1986); E. G. Sandstrom et al., *Lancet*, ii: 1480–1482 (1985); J. Gaub et al., *AIDS Res.*, 1:27–33 (1987); M. A. Jacobson, *J. Infect. Dis.*, 158:862–865 (1988); and C. V. Fletcher et al., *Antimicrob. Agents Chemother.*, 38:604–607 (1994). PFA also inhibits DNA polymerase from cytomegalovirus (CMV), herpes simplex virus (HSV) and other DNA viruses, and PFA has been particularly useful in treating cytomegalovirus. See B. Eriksson et al., *Biochim. Biophys. Acta*, 607:53–64 (1980); C. S. Crumpacker, *Am. J. Med.*, 92:3–7S (1992); O. Ringden et al., *Lancet, i*: 1502–1504 (1985); M. A. Jacobsen et al., *Antimicrob. Agents Chemother.*, 33:736–741 (1989); A. G. Palestine et al., *Ann. Intern. Med.*, 115:665–673 (1991); S. Safrin et al., *N. Engl. J. Med.*, 325:551–555 (1991); and M. M. Reddy, *J. Infect. Dis.*, 166:607–610 (1992). Phosphonoacetic acid (PAA, $HOOCCH_2P(=O)(OH)_2$) also exhibits antiviral activity. See U.S. Pat. No. 4,771,041 to Eriksson et al.

These known agents have well recognized limitations. For example, therapy with AZT (zidovudine), 3TC and other dideoxynucleosides has not prevented the breakdown of the immune system in many patients after a number of years of treatment. Still further, HIV strains have been reported that exhibit substantial resistance to AZT therapy and treatment with other known dideoxy nucleosides such as ddC, ddI, d4T and 3TC.

PFA does not have a high degree of oral absorption and consequently is generally administered intraveneously. PFA therapy also can result in toxicity to kidneys and hypocalcemia. Crisp et al., *Drugs*, 41:109–129 (1991).

Clinical resistance to PFA is known to occur after prolonged treatment. PFA resistant HIV-1 strains also have been produced in the laboratory by random as well as site-specific mutagenesis, and the pattern of cross resistance of such mutants to other reverse transcriptase inhibitors has been extensively analyzed. Mellors et al., *Antimicrobial Agents and Chemotherapy*, 39:1087–1092 (1995); Tachedjian et al., *J. Virol.*, 70:7171–7181 (1996).

Additionally, the triple negative charge of PFA at physiological pH is an impediment to cellular uptake. As a result, the PFA concentration needed to block viral replication in an intact cell or in vivo is orders of magnitude greater than the concentration needed to inhibit the enzyme in a cell-free assay. Further, in vivo clearance of PFA is very rapid, which makes longlasting control of viral infection difficult to achieve.

Certain PFA derivatives have been reported, including certain simple alkyl and aryl esters of the carboxyl and/or phosphonyl moiety of PFA, certain acyloxymethyl esters of the phosphonyl moiety as well as certain ester derivatives in which the carboxyl or phosphonyl group was joined to a nucleoside. See J. O. Noren et al., *J. Med. Chem.*, 26:264–270 (1983); L. R. Phillips et al., *Tetrahedron Letters*, 30:7141–7144 (1989); R. P. Iyer et al., *J. Pharm. Sci*, 83:1269–1273 (1994); M. Vaghefi et al., *J. Med. Chem.*, 29:1389–1393 (1986); H. Griengl et al., *J. Med. Chem.*, 31:1831–1839 (1988); A. Rosowsky et al., *Biochem. Biophys. Res. Commun.*, 172:288–294 (1990); J. Sahaet al., *Nucleosides & Nucleotides*, 10:1465–1475 (1991); and A. S. Charvet et al., *J. Med. Chem.*, 37:2216–2223 (1994). However, many of such compounds generally have not provided significant gains in terms of either potency or therapeutic selectivity for virally infected cells.

It thus would be desirable to have new compounds for treatment of virally infected cells, including cells infected with a retrovirus, particularly HIV. It would be especially desirable to have new compounds for treatment of cells infected with HIV strains that are resistant to current HIV therapeutics such as AZT and PFA.

SUMMARY OF THE INVENTION

We have discovered certain lipophilic phosphonoacid/nucleoside conjugates (covalently linked) that exhibit significant antiviral activity.

The invention thus provides methods of treatment against virus infections, including retroviral infections such as HIV infections, and treatment of other diseases caused by or otherwise associated with a virus such as influenza including influenza A and B; diseases associated with viruses of the herpes family, e.g., herpes simplex viruses (HSV) including herpes simplex 1 and 2 viruses (HSV 1, HSV 2), varicella zoster virus (VZV; shingles), human herpes virus 6, cytomegalovirus (CMV), Epstein-Barr virus (EBV), and other herpes virus infections such as feline herpes virus infections; diseases associated with hepatitis viruses including hepatitis B viruses (HBV); and the like.

Particularly preferred compounds of the invention are active against drug-resistant viral strains. Indeed, it has been surprisingly found that compounds of the invention are highly active against HIV strains that are PFA-resistant as well as HIV strains that are AZT-resistant.

Compounds of the invention include phosphonoacid/nucleoside conjugates where the carboxyl group and phosphonyl groups of the phosphonacid are esterified whereby the compound contains at least one lipophilic group and at least one nucleoside group. More specifically, the invention provides compounds of the following Formula I that are highly useful to treat viral infections:

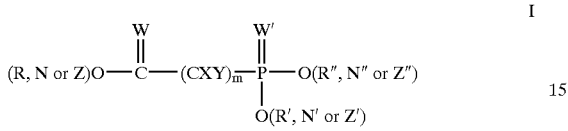

wherein at least one of R, R' and R" is present, and at least one of N, N' and N" is present;

each R, R' or R" are each independently an optionally substituted alkyl having from about 8 to 30 carbon atoms, preferably about 14 to 24 carbons; optionally substituted alkenyl having from about 8 to 30 carbon atoms, preferably about 14 to 24 carbons; optionally substituted alkynyl having from about 8 to 30 carbon atoms, preferably about 14 to 24 carbons; optionally substituted alkoxy having from about 8 to 30 carbon atoms, preferably about 14 to 24 carbons; optionally substituted alkylthio having from about 8 to 30 carbon atoms, preferably about 14 to 24 carbons; optionally substituted alkylsulfinyl having from about 8 to 30 carbon atoms, preferably about 14 to 24 carbons; optionally substituted alkylsulfonyl having from about 8 to 30 carbon atoms, preferably about 14 to 24 carbons; or optionally substituted alkylamino having from about 8 to 30 carbon atoms, preferably about 14 to 24 carbons;

X and Y (if present where m is 1) are each independently hydrogen; halogen; hydroxyl; sulfhydryl; amino; optionally substituted alkyl preferably having 1 to about 12 carbons, more preferably 1 to about 6 carbons; optionally substituted alkenyl preferably having from about 2 to 12 carbon atoms, more preferably about 2 to 6 carbons; optionally substituted alkynyl preferably having from about 2 to 12 carbon atoms, more preferably about 14 to 24 carbon atoms; optionally substituted alkoxy preferably having 1 to about 12 carbon atoms, more preferably 1 to about 6 carbon atoms; optionally substituted alkylthio preferably having from about 1 to 12 carbon atoms, more preferably about 1 to 6 carbon atoms; optionally substituted alkylsulfinyl preferably having from about 1 to 12 carbon atoms, more preferably about 1 to 6 carbon atoms; optionally substituted alkylsulfonyl preferably having from about 1 to 12 carbon atoms, more preferably about 1 to 6 carbon atoms; or optionally substituted alkylamino preferably having from about 1 to 12 carbon atoms, more preferably about 1 to 6 carbon atoms;

W and W' are the same or different and each is independently O, S or Se;

m is an integer equal to 0 or 1;

each Z, Z' and Z" is independently hydrogen or a pharmaceutically acceptable cation such as a sodium, potassium, lithium, ammonium or quaternary ammonium (e.g. $N(C_{1-6}\ alkyl)_4^+$), and Z also may be optionally substituted alkyl, alkenyl, alkynyl, alkoxy, alkylthio, alkylsulfinyl, alkylsulfonyl or alkylamino, such Z groups preferably having the number of carbon atoms as specified for corresponding X and Y groups; and each N, N' and N" is the same or different and is a nucleoside group, particularly a nucleoside group capable of exhibiting antiviral activity. Preferred nucleoside groups are those that in the triphosphate form are capable of selectively inhibiting a viral DNA or RNA polymerase, i.e. inhibiting a viral DNA or RNA polymerase selectively with respect to host cell polymerases. Suitable nucleoside groups include substituted or unsubstituted purine or pyrimidine bases typically containing a sugar group or a sugar derivative (e.g. a sugar derivative suitably may be an acyclic nucleoside side chain that contains one or more of each of hydroxy and/or alkoxy groups and about 2 to 10 carbons, more typically about 3 to 8 carbons, such as the —$CH_2OCH_2CH_2OH$ side chain of acyclovir or the —$CH_2OCH(CH_2OH)(CH_2OH)$ side chain of ganciclovir). Generally preferred nucleoside N groups include 2',3'-dideoxynucleosides or dioxanyl or thioxanyl analogues thereof, including those containing a purine or a pyrimidine base such as substituted and unsubstituted adenine, guanine, inosine, uracil, thymine, cytosine, etc. It also will be understood that in the above Formula I, the designation of "(R, N or Z)", "(R', N' or Z')" or "(R", N" or Z")" indicates that one of R, N or Z, or R', N' or Z' or R", N" or Z" respectively is present at the specified ester position. N, N' and N" nucleoside groups may be employed in racemic or optically active form, and the anomeric carbon may have either the α or β configuration.

Preferred compounds of Formula I include phosphonacid/nucleoside conjugates where the carboxyl group of phosphonoformic acid or phosphonoacetic acid is linked via a C-ester bond to a lipophilic group, and the phosphonyl moiety is linked via a P-ester bond to a nucleoside group. More specifically, preferred are compounds of the following Formula II:

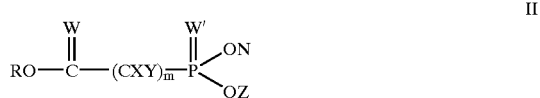

wherein R, X, Y, W, W', m, Z and N are as defined above for Formula I.

Generally preferred compounds of Formula II include those where m is 0, i.e. compounds of the following Formula IIA:

wherein R, W, W', Z and N are the same as defined above for Formula I.

Also preferred compounds of Formula I are compounds containing two nucleoside groups, including bis-nucleoside compounds of the following Formula III:

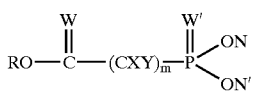

wherein R, W, W', X, Y and m are the same as defined above for Formula I; and N and N' are the same or different and are each a nucleoside as defined above for N of Formula I.

Generally preferred compounds of Formula III include conjugates of phosphonoformic acid derivatives, i.e. compounds of the following Formula IIIA:

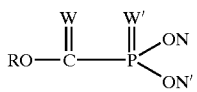

wherein R, W, W', N and N' are the same as defined for Formula III above.

Still further, also preferred are compounds of Formula I where the phosphonyl moiety is linked via a P-ester bond to a lipophilic group and either one or both of the carboxyl group and phosphonyl moiety of phophonoformic acid or phosphonoacetic acid is linked to a nucleoside group. In particular, compounds of the following Formula IV are provided:

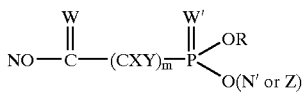

wherein N, N' W, W', X, Y, R, Z and m are the same as defined above for Formula I.

Generally preferred compounds of Formula IV include conjugates of phosphonoformic acid derivatives, i.e. compounds of the following Formula IVA:

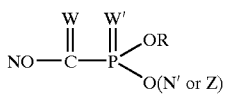

wherein N, N' W, W', R and Z are the same as defined above for IV. It is understood that in the above Formulae IV and IVA the designation of "(N' or Z)" indicates that one of N' and Z is present at the P-ester position.

Also preferred compounds of Formula I are the following compounds of Formula V:

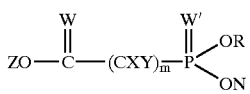

wherein Z, W, W' X, Y, R, N and m are the same as defined for Formula I.

Again, generally preferred compounds of Formula V include conjugates of phosphonoformic acid derivatives, i.e. compounds of the following Formula VA:

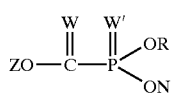

wherein Z, W, W', R, and N are the same as defined for Formula I.

As mentioned above, therapeutic compounds of the invention (i.e. compounds of Formulae I, IA, II, IIA, III, IIIA, IV, IVA, V and VA) are useful for treatment of viral infections, especially retroviral infections and in particular HIV infections, including treatment against HIV strains that exhibit resistance to current therapies. Compounds of the invention have been found to inhibit HIV-1 replication in cells infected with AZT-resistant HIV-1 strains as well as cells infected with PFA-resistant HIV-1 strains. Particularly preferred compounds of the invention exhibit $EC_{50}$ values of about 10 $\mu$M or less, and more preferably about 1 $\mu$M or less against AZT resistant HIV-1 strains (such as A018-post) and/or Foscarnet resistant HIV-1 strains (such as LAI-E89K) in standard HIV plaque reduction assays, specifically the HIV Plaque Reduction Assay of the protocol specified in Example 27 which follows. References herein to "HIV Plaque Reduction Assay" are intended to refer to the protocol of that Example 27.

The invention further provides pharmaceutical compositions that comprise one or more compounds of the invention and a suitable carrier. In a particularly preferred aspect, compounds of the invention are formulated as liposomes. The invention also provides compounds useful to prepare compounds of the invention. Other aspects of the invention are disclosed infra.

DETAILED DESCRIPTION OF THE INVENTION

We have now discovered that compounds of the following Formulae I, II, III, IV and V can be used to treat viral infections, particularly virally infected human cells, including cells infected with a retrovirus such as HIV, and thus the compounds can be used for treatment of HIV infected individuals:

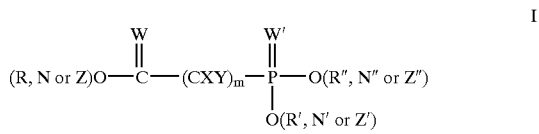

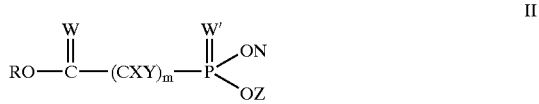

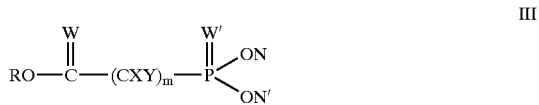

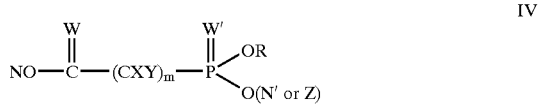

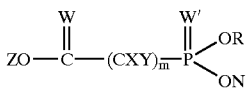

(V)

wherein R, R', R", W, W' X, Y, N, N', N", Z, Z', Z" and m are as defined above.

Optionally substituted alkyl, alkenyl, alkynyl, alkoxy and alkylthio, particularly non-cyclic alkyl, alkenyl, alkynyl, alkoxy and alkylthio, are generally preferred R groups of compounds of Formulae I, II, III, IV and V. Particularly suitable R groups include straight and branched chain alkyl, alkenyl, alkynyl, alkoxy and alkylthio optionally substituted by halogen, hydroxy and alkanoyl. Also suitable are R groups that contain one or more units of the following formula (A):

(A)

wherein each U is independently a sulfur, oxygen, optionally substituted nitrogen, sulfinyl (—SO—), or sulfonyl (—SO$_2$—);

$R^1$ and $R^2$ are each independently a hydrogen; halogen; nitro; optionally substituted alkyl having 1 to about 24 carbon atoms, more typically 1 to about 12 carbons; optionally substituted alkenyl having 2 to about 24 carbon atoms, more typically 2 to about 12 carbons; optionally substituted alkynyl having 2 to about 24 carbon atoms, more typically 2 to about 12 carbons; optionally substituted alkoxy having 1 to about 24 carbon atoms, more typically 1 to about 12 carbons; optionally substituted alkylamino having 1 to about 24 carbon atoms, more typically 1 to about 12 carbon atoms; or optionally substituted alkylthio having 1 to about 24 carbon atoms, more typically 1 to about 12 carbon atoms, or $R^2$ is a carbon atom and $R_1$ is a double or triple carbon-carbon bond to provide an alkenylene or alkynylene unit;

a is 0 or 1; b is 1 to about 30; and c is 0 or 1.

Particularly preferred R groups have the following formula (B):

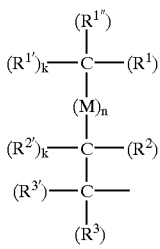

(B)

wherein $R^1$, $R^{1'}$ and $R^{1''}$ are each independently optionally substituted alkoxy group preferably having from 1 to about 24 carbon atoms; optionally substituted alkylthio group preferably having from 1 to about 24 carbon atoms; optionally substituted alkylsulfinyl group preferably having from 1 to about 24 carbon atoms; optionally substituted alkylsulfonyl group preferably having from 1 to about 24 carbon atoms; or optionally substituted alkanoyl preferably having from 1 to about 24 carbon atoms;

each k is independently 0 or 1;

each $R^2$ or $R^{2'}$ is independently hydrogen, =O, halogen, nitro, amino, methoxy, methylthio, —O-benzyl, —S-benzyl, amino substituted by alkanoyl having 1 to 24 carbon atoms and 0 to 3 double bonds, optionally substituted aminoalkyl having from 1 to 24 carbons and from 0 to 6 double bonds; and each M is independently —C($R^1$)($R^2$)— (wherein $R^1$ and $R^2$ are as defined in this formula (B) above) N, O, S, sulfinyl (SO) or sulfonyl (SO$_2$);

n is an integer of from 0 to 6;

$R^3$ and $R^{3'}$ are each independently hydrogen; halogen; hydroxyl; nitro; sulfhydryl; amino; optionally substituted alkyl preferably having 1 to about 24 carbon atoms; optionally substituted alkenyl preferably having 2 to about 24 carbon atoms; optionally substituted alkynyl preferably having 2 to about 24 carbon atoms; optionally substituted alkoxy preferably having 1 to about 24 carbon atoms; optionally substituted alkylthio preferably, having 1 to about 24 carbon atoms; optionally substituted alkylsulfinyl preferably having 1 to about 24 carbon atoms; optionally substituted alkylsulfonyl preferably having 1 to about 24 carbon atoms; or optionally substituted alkylamino preferably having 1 to about 24 carbon atoms. (It is understood that the carbon of formulae (B) with $R^3$ and $R^{3'}$ is directly bonded to the conjugate molecule.)

Additional preferred R groups of compounds of the invention have the following formula (C):

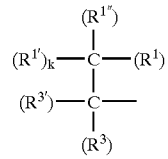

(C)

wherein $R^1$, $R^{1'}$, $R^{1''}$, k, $R^3$ and $R^{3'}$ are each the same as defined above for formula (B). (It is understood that the carbon of formulae (C) with $R^3$ and $R^{3'}$ is directly bonded to the conjugate molecule.)

Particularly preferred nucleosides groups (i.e. N, N'or N" groups) of compounds of the invention include 2',3'-dideoxynucleosides, especially 3'-azido-3'-deoxythymidine (AZT), and other 2',3'-dideoxynucleosides such as 2',3'-dideoxyinosine (ddI), 2'-fluoro-2',3'-dideoxyinosine (F-ddI), 2',3'-dideoxycytidine (ddC), 2'-fluoro-2',3'-dideoxyadenosine (F-ddA), 5-fluoro-3'-thia-2',3'-dideoxycytidine, trifluridine (Merck Index, 11th edition, 9599), d4T (stavudine), 3TC (lamivudine), vidarabine (Merck Index, 11th edition, 9881), idoxuridine (Merck Index, 11th edition, 4819), (−)-fialuridine ((−)-FIAU; (−)-1',2'-deoxy-2'-fluoro-1-β-D-arabinofuranosyl-5-iodouracil), d4T, 3TC, 1592U89, sorivudine (BV-araU), (+), (−) or (±) FTC ((+), (−) or (±) 5-fluoro-1-2-(hydroxymethyl)-(1,3-oxathiolan-5-yl)cytosine), β-D-2,6-diaminopurine-dioxolanyl (DAPD), and 2',3'-dideoxy-3'-azido-5-methylcytidine (CS92). Acyclovir, ganciclovir and penciclovir ((9-[4-hydroxy-3-(hydroxymethylbut-1-yl] guanine) are also preferred nucleoside groups of compounds of the invention. A nucleoside group (N, N' or N") is suitably covalently linked to a conjugate of the invention at the site of a hydroxyl group of a sugar or sugar derivative of the nucleoside group (e.g. as exemplified in the Schemes which follow), although other linkages at other positions of a nucleoside group also will be suitable.

Preferred Z groups of compounds of Formulae I, II, III, IV and V include physiologically acceptable cations such as an ammonium or quaternary ammonium cation. Oxygen is a typically preferred W and/or W' group of compounds of Formulae I, II, III, IV and V. Compounds where at least one of W and W' is sulfur also will be preferred.

Suitable halogen substituent groups of compounds of the invention are F, Cl, Br and I. As used herein, the term alkyl unless otherwise modified refers to both cyclic and noncyclic groups, although cyclic groups will comprise at least three carbon ring atoms. Alicyclic alkyl groups are generally preferred. Alkenyl and alkynyl groups of compounds of the invention have one or more unsaturated linkages, typically 1 to about 3 or 4 unsaturated linkages. Also, the terms alkenyl and alkynyl as used herein refer to both cyclic and noncyclic groups, although straight or branched noncyclic groups are generally more preferred. Alkoxy groups of compounds of the invention have one or more oxygen linkages, typically 1 to about 5 or 6 oxygen linkages. Alkylthio groups of compounds of the invention have one or more thioether linkages, typically 1 to about 5 or 6 thioether linkages. Alkylsulfinyl groups of compound of the invention have one or more sulfinyl (SO) linkages, typically 1 to about 5 or 6 sulfinyl linkages. Alkylsulfonyl groups of compounds of the invention have one or more sulfonyl ($SO_2$) linkages, typically 1 to about 5 or 6 sulfonyl linkages. Preferred alkylamino groups of compounds of the invention include those groups having one or more primary, secondary and/or tertiary amine groups, preferably 1 to about 3 or 4 amine groups. Suitable alkanoyl groups have one or more carbonyl groups, typically 1 to about 4 or 5 carbonyl groups. Alkoxy, alkylthio, alkylsulfinyl, alkylsulfonyl, alkanoyl and other groups may be suitably either linear or branched.

As discussed above, R, R', R" (including R, R', R" groups of formulae (A), (B) and (C)), X, Y, Z, nucleoside and other groups are optionally substituted. Suitable groups that may be present on a "substituted" R, R', R", X, Y, Z, nucleoside or other substituent include e.g. halogen such as fluoro, chloro, bromo and iodo; cyano; hydroxyl; nitro; azido; sulfhydryl; alkanoyl e.g. $C_{1-6}$ alkanoyl group such as acetyl and the like; carboxamido; alkyl groups including those groups having 1 to about 12 carbon atoms, preferably from 1 to about 6 carbon atoms; alkenyl and alkynyl groups including groups having one or more unsaturated linkages and from 2 to about 12 carbon atoms, preferably from 2 to about 6 carbon atoms; alkoxy groups having one or more oxygen linkages and from 1 to about 12 carbon atoms, preferably 1 to about 6 carbon atoms; aryloxy such as phenoxy; alkylthio groups including those moieties having one or more thioether linkages and from 1 to about 12 carbon atoms, preferably from 1 to about 6 carbon atoms; alkylsulfinyl groups including those moieties having one or more sulfonyl linkages and from 1 to about 12 carbon atoms, preferably from 1 to about 6 carbon atoms; alkylsulfonyl groups including those moieties having one or more sulfonyl linkages and from 1 to about 12 carbon atoms, preferably from 1 to about 6 carbon atoms; aminoalkyl groups such as groups having one or more N atoms and from 1 to about 12 carbon atoms, preferably from 1 to about 6 carbon atoms; carbocyclic aryl having 6 or more carbons, particularly phenyl; aryloxy such as phenoxy; aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl. A "substituted" R, R' R", X, Y, Z, nucleoside or other substituent of a compound of the invention may be substituted at one or more available positions, typically 1 to about 3 positions, by one or more suitable groups such as those listed immediately above.

It was also indicated that in Formula (A), U may be substituted to provide a tertiary amine. Such a substituted nitrogen may be substituted by suitable groups set forth above with respect to other substituted groups, particularly substitutions of alkyl, alkoxy, alkylthio and aminoalkyl groups.

Specifically preferred compounds of the invention include:

3'-azido-3'-deoxy-5'-O-(1-octadecyloxycarbonyloxyphosphinyl)thymidine;
3'-azido-3'-deoxy-5'-O-(1-eicosanyloxycarbonyloxyphosphinyl)thymidine;
3'-azido-3'-deoxy-5'-O-(1-docosanyloxycarbonyloxyphosphinyl)thymidine;
3'-azido-3'-deoxy-5'-O-[(3β-cholest-5-enyl)oxycarbonyloxyphosphinyl)]thymidine;
di-O-(3'-azido-3'-deoxythimidin-5'-yl)-1-octadecyloxycarbonylphosphonate;
di-O-(3'-azido-3'-deoxythimidin-5'-yl)-1-eicosanyloxycarbonylphosphonate;
di-O-(3'-azido-3'-deoxythimidin-5'-yl)-1-docosanyloxycarbonylphosphonate;
di-O-(3'-azido-3'-deoxythimidin-5'-yl)-3β-cholest-5-enyloxycarbonylphosphonate; sodium 3'-azido-3'-deoxy-5'-O-(hexadecyloxypropoxy)carbonyloxyphosphinyl thymidine; and 3'-azido-3'-deoxy-5'-O-[(hexadecyloxypropoxy) (hydroxy)phosphono(carbonyl] thymidine.

In certain preferred aspects, the invention includes compounds of Formulae II' and IIA', which are defined the same as above for Formulae II and IIA respectively, except that the group R does not contain heteroatoms (N, O, S), or at least the group R does not contain oxygen or thio substitution. Compounds of Formula II' and IIA' can be used in the therapeutic methods disclosed herein including to treat viral infections, particularly cells infected with HIV and drug-resistant HIV strains.

As mentioned above, the invention also includes novel intermediate compounds useful to prepare compounds the invention. Specifically, chloroformates of the following Formula VI are provided:

VI wherein R is as defined above in Formula I.

Additional intermediate compounds of the invention are carbonylphosphonic acids of the following Formula VII:

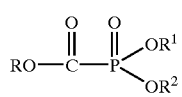

VII wherein R is the same as defined above for Formula I; and $R^1$ and $R^2$ may be the same or different and are hydrogen; a counter cation e.g. a pharmaceutically acceptable cation such as an alkali metal or earth metal, e.g. sodium, potassium, lithium, etc., or an ammonium or quaternary ammonium cation (e.g. $NZ_4^+$ where Z is $C_{1-4}$ alkyl); or alkyl, preferably having 1 to about 12 carbons, more preferably 1 to about 3 carbons.

Compounds of Formula VII also may be used in the therapeutic methods disclosed herein, including to treat viral infections, particularly cells infected with HIV.

Compounds of the invention can be prepared as generally depicted in the following Schemes I through VI. In the discussions of those Schemes, the group R is the same as defined above for Formulae I, II, III, IV and V. Additionally, for purposes of exemplification only, a preferred nucleoside (group N, N', N" in Formulae I through V) of AZT is depicted in the Schemes, and it will be understood that a wide variety of nucleosides can be employed in the same manner as discussed below for AZT. Similarly, compounds exemplified in the Schemes are phosphonoformic acid derivatives, i.e. compounds of Formulae I, II, III, IV and V (and corresponding intermediates) where m is 0, although other phosphonoacid derivatives can be similarly employed to provide compounds of Formulae I–V where m=1. Compounds of the invention where W and/or W' is sulfur or Se also can be prepared as shown in the following Schemes with substitution of appropriate starting materials, e.g. a thio or selenium reagent. See, for instance, WO 96/39831.

SCHEME I

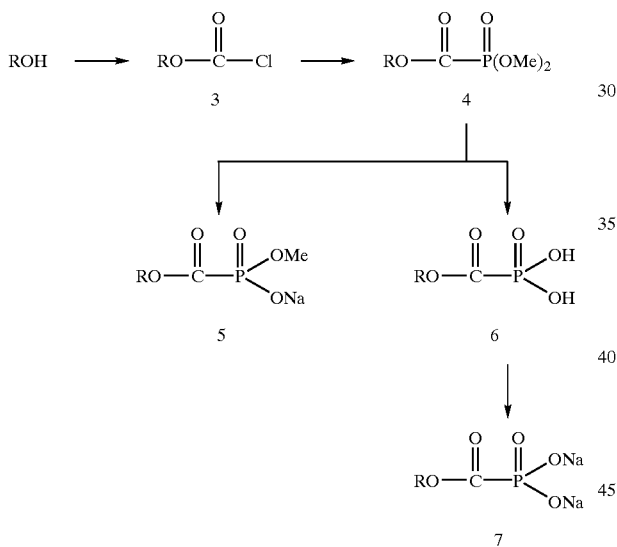

As shown in Scheme I, for preparation of compounds of Formulae I, II and III of the invention, a carbonylphosphonate 4 is suitably prepared by reaction of the corresponding alcohol ROH with phosgene or triphosgene $((Cl_3CO)_2CO)$ to provide the chloroformate 3. See Examples 1–3 which follow for exemplary reaction conditions. Arbuzov reaction of 3 with a trialkyl phosphite such as trimethylphosphite yields the triester 4. See Examples 4–7 which follow for exemplary conditions.

Selective removal of one alkyl group by overnight treatment of the triester 4 with NaI in a suitable solvent such as dimethylformamide with or without tetrahydrofuran or acetone as a co-solvent provides the diester 5 in generally good yields with generally little or no purification required other than washing with hexane or other suitable solvent to remove any unreacted starting material. See Examples 8–11 which follow.

Treatment of triester 4 with $Me_3SiBr$ in a suitable solvent such as methylene chloride for a time and temperature sufficient for reaction completion (e.g. room temperature for about four hours) provides phosphonic acid 6. See Examples 12–15 which follow. The phosphonic acid 6 typically will be highly hygroscopic and should be stored appropriately, e.g. −20° C. in a tightly sealed container. The acid 6 can be converted to the corresponding salt 7, e.g. by treatment with two molar equivalents of NaOMe in methanol. See Examples 16–19 which follow.

As depicted in Schemes II through IV below, compounds of Formulae I, II and III can be prepared by several routes from the above discussed intermediates. Thus, as shown in the following Scheme II, triester 4 is reacted with excess $PCl_5$ in a suitable solvent and for a time and temperature sufficient to form monochloro intermediate 8, e.g. in refluxing $CCl_4$ for three hours under an inert atmosphere such as dry argon. Excess $PCl_5$ can be destroyed by bubbling $SO_2$ gas through the reaction mixture. The resulting reaction mixture can be evaporated to dryness under reduced pressure, the residue of 8 taken up in a suitable solvent such as dry dimethylformamide and cooled to −50° C. or other suitable temperature. The nucleoside reagent in moderate molar excess (e.g. 1.5 molar equivalents) is then added to the solution and the mixture stirred for a time and temperature sufficient for reaction completion, e.g. for 24 hours at room temperature. See Method A of Example 20 for an exemplary procedure. The resulting compound 9 can be purified e.g. by flash chromatography and optionally further reacted to provide other compounds of the invention. For example, the P—OCH$_3$ ester 9 shown in Scheme II below can be treated at room temperature for 24 hours with about 1.4 to 1.5 equivalents of NaI in tetrahydrofuran under argon in the absence of light followed by ion-chromatography on DEAE-cellulose with $NH_4HCO_3$ as the eluent to provide compound 10 where X is $ONH_4$.

SCHEME II

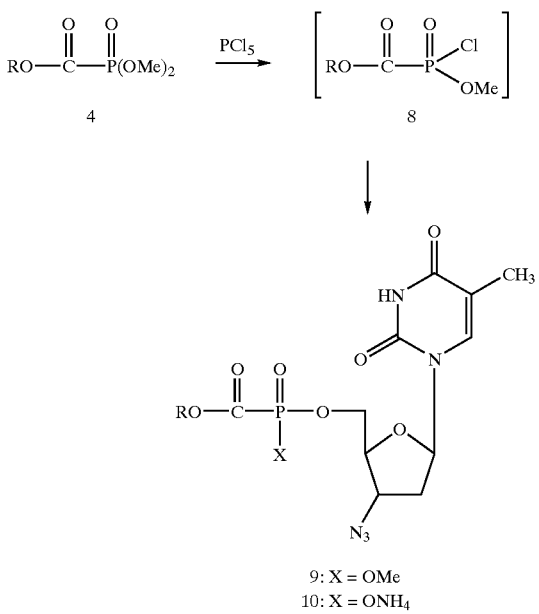

9: X = OMe
10: X = ONH$_4$

Compounds of Formula III can be prepared in similar manner as shown in Scheme II above with modification of reaction conditions to favor formation of the bis-nucleoside conjugate. Thus, for example, as shown in Scheme III below, triester 4 is reacted with excess $PCl_5$ in a suitable solvent and for a time and temperature sufficient to form the dichloro intermediate 11, for example in refluxing $CCl_4$ for 48 hours under an inert atmosphere such as dry argon. Intermediate 11 is then reacted with a relatively large molar excess of one or more nucleoside reagents and for extended periods, e.g. with about 3 molar equivalents of AZT for 48 hours, to provide bis-nucleoside compound 12. See Example 24 for exemplary reaction conditions.

mula I can be further reacted to provide other compounds of the invention, e.g. flash chromatography on silica gel with 85:15:1 $CHCl_3$—MeOH-28%$NH_4OH$ as the eluent to provide compound 10 (i.e. X=$ONH_4$). This $Cl_3CCN$ method is generally preferred as a more direct route that can provide higher overall yields than the above discussed $PCl_5$ procedure.

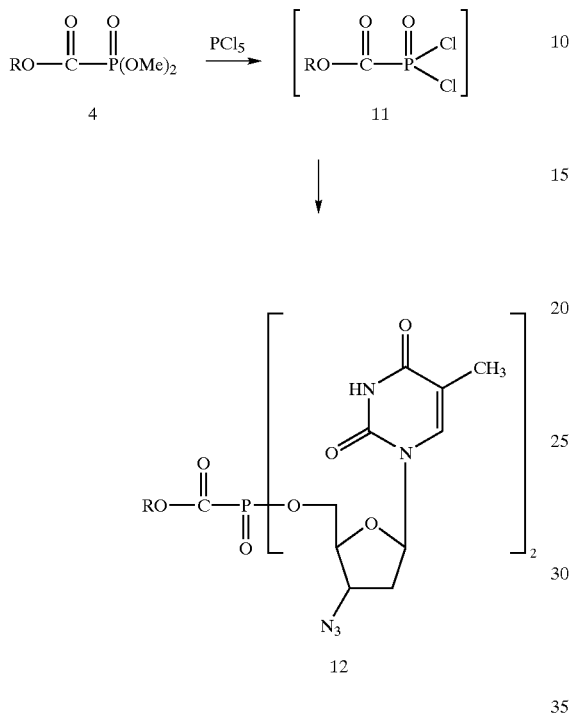

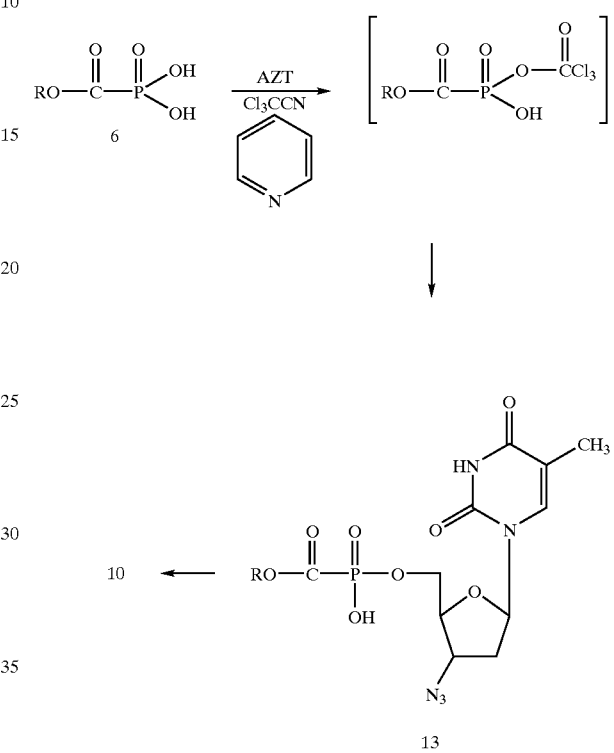

An alternative route to compounds of Formulae I through III is generally shown in Scheme IV below. Intermediate 5 is reacted with an excess of the nucleoside reagent and $Cl_3CCN$ in pyridine for a time and temperature sufficient for reaction completion, e.g. reaction with excess AZT under argon at about 50 to 60° C. overnight, and with the rigorous exclusion of moisture. See Method B of Example 20 for an exemplary procedure. The resulting compound 13 of For- Compounds of the invention having structures of Formulae IV are suitably prepared as generally depicted in the following Schemes V and VI.

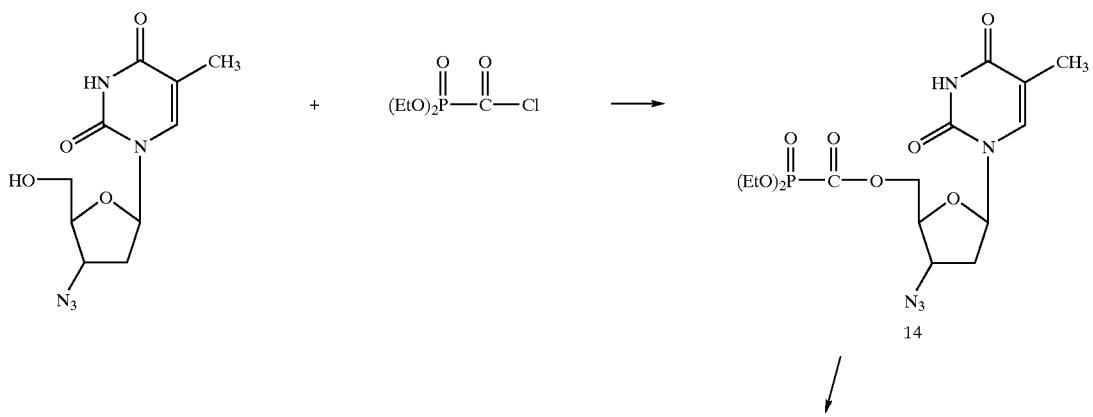

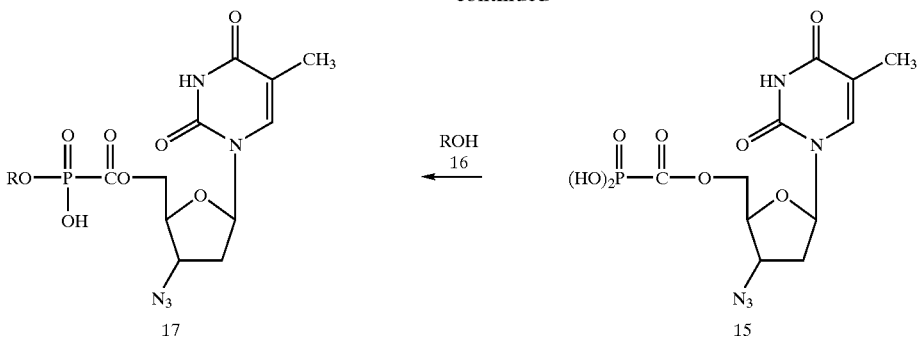

Thus, as shown in Scheme V, carbonyl nucleoside ester 14 is prepared by reaction of a dialkylphosphonoformic chloride with a desired nucleoside, e.g. AZT as shown above, under suitable conditions such as addition of a pyridine solution of diethylphosphonoformic chloride to a solution of the nucleoside in pyridine suitably in the presence of a catalyst such as N,N-dimethylaminopyridine followed by overnight stirring of the reaction mixture. See Example 25, Part A for exemplary conditions. Treatment of triester 14 with $Me_3SiBr$ in a suitable solvent such as dry acetonitrile for a time and temperature sufficient for reaction completion provides the diacid 15 which can be isolated under reduced pressure and used for further reaction without additional purification. Thus, the isolated diacid 15 can be reacted with a lipophilic alcohol 16 to provide the P-ester 17 in the presence of a coupling agent. See, for instance, Example 25.

Scheme VI depicts a suitable preparation of additional compounds of Formula V.

SCHEME VI

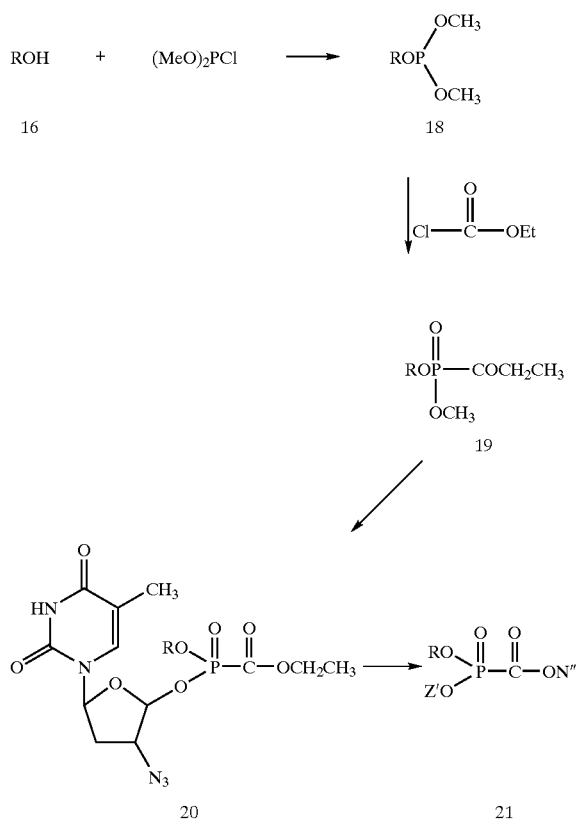

Thus, as shown in Scheme VI, lipophilic alcohol 16 is reacted with a dialkylphosphorochloridite in the presence of base to provide the lipophilic phosphite 18, which can be purified as desired e.g. by flash chromatography. The phosphite 18 is then reacted with an alkyl chloroformate to provide phosphonate 19. Treatment of the phosphonate 19 with a slight molar excess of $PCl_5$ in a suitable solvent and for a time and temperature sufficient to form a reactive phosphonyl chloride intermediate. Suitable reaction conditions include refluxing the phosphonate 19 and $PCl_5$ in $CCl_4$ for about three hours or more. Excess $PCl_5$ can be destroyed by bubbling $SO_2$ gas through the reaction mixture. The phosphonyl chloride intermediate can be isolated under reduced pressure and the resulting residue taken up in dry dimethylformamide or other suitable solvent and cooled to −50° C. or other suitable temperature. The nucleoside reagent is then added to the phosphonyl chloride solution and the resulting mixture stirred for a time and temperature sufficient for reaction completion, e.g. for about 24 hours at room temperature. The resulting triester conjugate 20 can be purified as desired, e.g. by flash chromatography. See Example 26, Part C for an exemplary procedure. The conjugate 20 is further reacted to provide compounds of the invention, e.g. the triester 20 can be hydrolyzed under basic conditions to provide a carboxy salt 21, i.e. where N" of 21 is a pharmaceutically acceptable cation. That salt or the chloroformate derivative thereof (i.e. the compound RO(NO)P(=O)C(=O)Cl) then can be reacted with a nucleoside reagent such as AZT to provide the bis-nucleoside compound 21 where N' is a nucleoside group.

As discussed above, the invention includes methods for synthesis of the compounds of the invention. Thus, the invention includes methods for preparation of compounds of Formula III which includes reacting a carbonylphosphonic acid or carbonylphosphonic acid halide such as an acid di-halide 11 shown in Scheme III above with a molar excess of a nucleoside, preferably about a two or 2.5 or more molar excess of a nucleoside at a time and temperature suitable for reaction. The invention also includes methods for preparation of compounds of Formulae II and III by reaction of a phosphonic acid substituted by a lipophilic R group (e.g. intermediate 5 of Scheme IV) with a nucleoside (preferably used in molar excess) and $Cl_3CCN$, preferably in a suitable solvent such as a pyridine, for a time and temperature sufficient for reaction completion.

The invention thus provides methods of treatment against virus infections and diseases associated with viruses, which methods in general will comprise administration of a therapeutically effective amount of one or more compounds of Formulae I, II, III, IV or V to a mammal, particularly a human, suffering from or susceptible to a viral infection or disease otherwise associated with a virus.

Compounds of the invention will be useful to treat cells infected with a virus capable of causing an immunodeficiency disease, particularly in a human. Compounds of the invention will be particularly useful to treat retroviral infection in cells and in a human, particularly HIV infected human cells. Specific examples of retroviral infections which may be treated in accordance with the invention include human retroviral infections such as HIV-1, HIV-2, and Human T-cell Lymphotropic Virus (HTLV) e.g. HTLV-I or HTLV-II infections.

The invention also provides methods of treatment of other diseases caused by or otherwise associated with a virus such as influenza including influenza A and B as well as diseases associated with viruses of the herpes family, e.g., herpes simplex viruses (HSV) including herpes simplex 1 and 2 viruses (HSV 1, HSV 2), varicella zoster virus (VZV; shingles), human herpes virus 6, cytomegalovirus (CMV), Epstein-Barr virus (EBV), and other herpes virus infections such as feline herpes virus infections, and diseases associated with hepatitis viruses including hepatitis B viruses (HBV) B virus. Examples of clinical conditions which are caused by such viruses include herpetic keratitis, herpetic encephalitis, cold sores and genital infections (caused by herpes simplex), chicken pox and shingles (caused by varicella zoster) and CMV-pneumonia and retinitis, particularly in immunocompromised patients including renal and bone marrow transplant patients and patients with Acquired Immune Deficiency Syndrome (AIDS). Epstein-Barr virus can cause infectious mononucleosis, and is also suggested as the causative agent of nasopharyngeal cancer, immunoblastic lymphoma and Burkitt's lymphoma.

As discussed above, particularly preferred compounds of the invention are active against drug-resistant viral strains, and it has been surprisingly found that compounds of the invention are highly active against HIV strains that are PFA-resistant as well as HIV strains that are AZT-resistant.

Without wishing to be bound by theory, it is believed the multiple and distinct covalently linked antiviral agents (i.e. a nucleoside and a phosphonoacid) of compounds of the invention make it more difficult for a virus to successfully mutate to any one of the linked agents.

Moreover, by virtue of the covalent linkage, the conjugates of the invention present the nucleoside and phosphonacid compounds to a virus essentially simultaneously, an effect that may not be readily achieved by administering the same compounds in a drug "cocktail" formulation without covalently linking the compounds.

It also has been reported that treatment with a 2',3'-dideoxynucleoside such as AZT can sensitize a patient to Foscarnet, and treatment with Foscarnet can in turn sensitize a patient to a 2',3'-dideoxynucleoside such as AZT. See G. Tachedjian et al., *Virology*, 212:58–62 (1995); and G. Tachedjian et al., *Virology*, 70:7171–7181 (1996). Accordingly, the essentially simultaneous presentation to a virally infected cell of a nucleoside and phosphonacid via a conjugate of the invention may provide synergistic results, as is indicated by the data shown in the examples which follow, including Example 28.

Administration of compounds of the invention may be made by a variety of suitable routes including oral, topical (including transdermal, buccal or sublingual), nasal and parenteral (including intraperitoneal, subcutaneous, intravenous, intradermal or intramuscular injection) with oral or parenteral being generally preferred. It also will be appreciated that the preferred method of administration and dosage amount may vary with, for example, the condition and age of the recipient.

Compounds of the invention may be used in therapy in conjunction with other medicaments such as reverse transcriptase inhibitors such as a dideoxynucleoside including AZT, ddI, ddC, d4T, 3TC, FTC, DAPD, 1592U89 or CS92; TAT antagonists such as Ro 3-3335 and Ro 24-7429; protease inhibitors such as saquinavir, ritonavir, indinavir or AG1343 (Viracept); and other agents such as 9-(2-hydroxyethoxymethyl)guanine (acyclovir), ganciclovir or penciclovir, interferon, e.g., alpha-interon or interleukin II, or in conjunction with other immune modulation agents including bone marrow or lymphocyte transplants or other medications such as levamisol or thymosin which would increase lymphocyte numbers and/or function as is appropriate.

While one or more compounds of the invention may be administered alone, they also may be present as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Therapeutic compounds of the invention also may be incorporated into liposomes. The incorporation can be carried out according to known liposome preparation procedures, e.g. sonication and extrusion. Suitable conventional methods of liposome preparation are also disclosed in e.g. A. D. Bangham et al., *J. Mol. Biol.*, 23:238–252 (1965); F. Olson et al., *Biochim. Biophys. Acta*, 557:9–23 (1979); F. Szoka et al., *Proc. Nat. Acad. Sci.*, 75:4194–4198 (1978); S. Kim et al., *Biochim. Biophys. Acta*, 728:339–348 (1983); and Mayer et al., *Biochim. Biophys. Acta*, 858:161–168 (1986).

The liposome may be made from one or more of the conjugates of Formulae I–V alone, or more preferably, in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine or phosphatidylinositol. Synthetic phospholipids also may be used e.g., dimyristoylphosphatidylcholine, dioleoylphosphatidylcholine, dioleoylphosphatidycholine and corresponding synthetic phosphatidylethanolamines and phosphatidylglycerols. Cholesterol or other sterols, cholesterol hemisuccinate, glycolipids, 1,2-bis(oleoyloxy)-3-(trimethyl ammonio)propane (DOTAP), N-[1-(2,3-dioleoyl)propyl]-N,N,N-trimethylammonium chloride (DOTMA), and other cationic lipids may be incorporated into the liposomes. The relative amounts of the one or more compounds of Formulae I–V and additives used in the liposomes may vary relatively widely. Liposomes of the invention suitably contain about 60 to 90 mole percent of natural or synthetic phospholipid; cholesterol, cholesterol hemisuccinate, fatty acids or cationic lipids may be used in amounts ranging from 0 to 50 mole percent; and the one or more therapeutic compounds of the invention may be suitably present in amounts of from about 0.01 to about 50 mole percent.

Additionally, the lipophilic R groups of compounds of the invention can enable preparation of liposomes where compound(s) of Formulae I–V are substantially incorporated into the lipid bilayer of a liposome and the aqueous liposome compartment may contain one or more other drugs such as an antiviral nucleoside (preferably AZT, ddI, ddC, d4T, 3TC or 1592U89) or other of the antiviral agents discussed above to provide an effective "cocktail" formulation system.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, for treatment of immunodeficiency infections, particularly an HIV infection, a suitable effective dose of one or more compounds of Formulae I, II, III, IV or V will be in the range of from 0.01 to 100 milligrams per kilogram of bodyweight of recipient per day, preferably in the range of from 0.1 to 50 milligrams per kilogram bodyweight of recipient per day, more preferably in the range of 1 to 20 milligrams per kilogram bodyweight of recipient per day. The desired dose is suitably administered once daily, or several sub-doses, e.g. 2 to 5 sub-doses, are administered at appropriate intervals through the day, or other appropriate schedule.

All documents mentioned herein are incorporated herein by reference.

The present invention is further illustrated by the following examples. These examples are provided to aid in the understanding of the invention and are not to be construed as limitations thereof.

In the following examples 1–24, IR spectra were obtained on a Perkin-Elmer Model 781 double-beam recording spectrophotometer; $^1$H NMR spectra were obtained on Varian Model EM360L and Bruker AM-500 instruments at 60 and 500 MHz, respectively, with $Me_4Si$ as the reference. TLC was performed on Whatman MK6F and Baker 250F silica gel plates with a fluorescent indicator dye. Spots were visualized under a 254-nm UV lamp, in an iodine chamber, or by spraying with $H_2SO_4/H_2O/EtOH$ or molybdic acid spray reagent. Melting points were obtained on a Fisher-Johns hot-stage apparatus and are not corrected. Chemicals were purchased from Aldrich (Milwaukee, Wis.), Sigma (St. Louis, Mo.), and Fisher (Boston, Mass.). Solvents were routinely stored over Linde 4Å molecular sieves. Microchemical analyses were done by Quantitative Technologies, Inc., Whitehouse, N.J.

EXAMPLE 1

Preparation of 1-octadecyl chloroformate (Formula VI: $R=CH_3(CH_2)_{17}-$)

Method A. A solution of 1-octadecanol (6.0 g, 22 mmol) in a mixture of toluene (240 mL) and $Et_2O$(120 mL) was added dropwise to a stirred, ice-cold solution of 20% phosgene in toluene (26.7 mL, 50 mmol) over 30 minutes. The reaction mixture was allowed to come to room temperature, and stirring was continued under an argon atmosphere for 2 hours. Evaporation at water aspirator pressure followed by trituration with $Et_2O$, suction filtration and drying yielded a waxy white solid (7.12 g, 97%); mp 30–32° C.; IR (KBr): υ 2950–2900, 2850, 1780, 1455, 1375 $cm^{-1}$; $^1$H NMR ($CDCl_3$) δ0.7–1.9 (m, 35H, $CH_3(CH_2)_{16}$), 4.3(t, 2H, $CH_2O$). Anal. Calcd. for $C_{19}H_{37}ClO_2$: C, 68.52; H, 11.22; Cl, 10.65. Found: C, 68.24; H, 10.98; Cl, 10.23.

Method B. Solid triphosgene (2.7 g, 9.1 mmol) was added to a stirred solution of 1-octadecanol (5.0 g, 1.8 mmol) and dry pyridine (0.15 g, 1.9 mmol) in dry $CCl_4$ (20 mL) cooled in an ice-salt mixture. After 5 minutes at −15° C., the mixture was allowed to come to room temperature, stirred for 1.5 hours, and finally warmed to 40° C. in a water bath and stirred overnight at room temperature. After filtration of the pyridinium chloride salt, the solvent was evaporated to obtain a colorless gum indistinguishable from the triester obtained by Method A above; yield 6 g (99%)

EXAMPLE 2

Preparation of 1-eicosanyl chloroformate (Formula VI: $R=CH_3(CH_2)_{19}-$)

The same methods as described for Example 1 were employed using 1-eicosanol to provide the title compound as a waxy white solid from which traces of toluene were not fully removed (95% yield); mp 33–34° C.; TLC: $R_f$ 0.49 (silica gel, 98:2 $CHCl_3$-MeOH); IR (KBr): υ 2980–2890–2850, 1780, 1470, 1380, 1300, 1215 $cm^{-1}$; NMR ($CDCl_3$) δ0.8–1.6 (m, 39H, $CH_3(CH_2)_{18}$), 4.3 (t, 2H, $CH_2O$). Anal. Calcd. for $C_{12}H_{41}ClO_2.0.1C_6H_5CH_3$: H, 70.38; H, 11.40; Cl, 9.57. Found: C, 70.69; H 11.28; Cl, 9.49.

EXAMPLE 3

Preparation of 1-docosanyl chloroformate (Formula VI: $R=CH_3(CH_2)_{21}-$)

A mixture of 1-docosanol (3.3 g, 10 mmol) in a mixture of toluene (25 mL), $CH_2Cl_2$(25 mL), and $Et_2O$(25 mL) was warmed to 30–35° C. to obtain a clear solution which was then added dropwise to an ice-cold solution of 20% phosgene (15.0 mL, 28 mmol) in toluene over 10 minutes workup as described in Example 1 above to yield a waxy white solid (3.82 g, 98%); mp 39–40° C.; TLC: $R_{f1}$ 0.50 (silica gel, 98:2 $CHCl_3$—MeOH); IR (KBr): υ 2960–2900, 2860, 1780, 1470, 1360, 1300, 1265 cm$^{-1}$; $^1$H NMR (CDCl$_3$) δ0.8–1.8 (m, 43H, CH$_3$(CH$_2$)$_{20}$), 4.3 (t, 2H, CH$_2$O). Anal. Calcd. for C$_{23}$H$_{45}$ClO$_2$: C, 70.99; H, 11.68; Cl, 9.11. Found: C, 71.31; H, 11.63; Cl, 8.90.

EXAMPLE 4

Preparation of dimethyl 1-octadecyloxycarbonylphosphonate (Formula VII: R=CH$_3$(CH$_2$)$_{17}$—, R$^1$=R$^2$=CH$_3$)

A mixture of octadecyl chloroformate (7.0 g, 21 mmol) and P(OMe)$_3$ (37.2 mL) was stirred at 80° C. for 2 hours and allowed to cool overnight. The white solid of the title compound which formed was collected, washed with hexane, and dried overnight in a vacuum oven; yield 6.0 g. A second crop was obtained from the filtrate upon cooling (2.1 g); total yield 8.1 g (95%); mp 41–42° C. (hexane); IR (KBr): υ 2950–2880, 2830, 1710, 1470, 1375, 1350, 1280, 1220 cm$^{-1}$; $^1$H NMR (CDCl$_3$) δ 0.8–1.8 (m, 35H, CH$_3$(CH$_2$)$_{16}$), 3.9 (d, 6H, P(OCH$_3$)$_2$), 4.3 (t, 2H, CH$_2$O). Anal. Calcd. for C$_{21}$H$_{43}$O$_5$P: C, 62.03; H, 10.68; P, 7.62. Found: C, 62.16; H, 10/71; P, 7.69.

EXAMPLE 5

Preparation of Dimethyl 1-eicosanyloxycarbonylphosphonate (Formula VII: R=CH$_3$(CH$_2$)$_{19}$—, R$^1$=R$^2$=CH$_3$)

1-Eicosanyl chloroformate (6.0 g, 16.6 mmol) was added slowly to refluxing P(OMe)$_3$ 30 (mL), and after 2 hours the mixture was left at room temperature overnight. Excess P(OMe)$_3$ was removed by vacuum distillation, and the remaining white solid was collected, washed with cold hexane, and recrystallized from hexane to obtain colorless crystals from which traces of hexane were not fully removed (7.0 g, 97% yield); mp 53–54° C.; TLC: R$_f$ 0.39 (silica gel, 98:2 CHCl$_3$—MeOH); IR (KBr): υ 2950, 2915, 1705, 1540, 1280, 1220 cm$^{-1}$; $^1$H NMR (CDCl$_3$) δ0.8–1.8 (m, >39H, CH$_3$(CH$_2$)$_{18}$), 3.9 (d, 6H, P(OCH$_3$)$_2$), 4.3 (t, 2H, CH$_2$O). Anal. Calcd. for C$_{23}$H$_{47}$O$_5$P.0.15C$_6$H$_{14}$: C, 64.13, H, 11.08; P, 6.92. Found: C, 63.91; H, 10.91; P, 6.62.

EXAMPLE 6

Preparation of Dimethyl 1-docosanyloxycarbonylphosphonate (Formula VII: R=CH$_3$(CH$_2$)$_{21}$—, R$^1$=R$^2$=CH$_3$)

The title compound was prepared using docosanyl chloroformate and worked up as described in Example 5, 85% yield (including a trace of residual hexane); mp 60–61° C.; TLC: R$_f$ 0.49 (silica gel, 98:2 CHCl3—MeOH); IR (KBr): υ 2960, 2910, 2850, 1710, 1470, 1285, 1225 cm$^{-1}$; $^1$H NMR (CDCl$_3$) δ0.8–2.8 (m, >43H, CH$_3$(CH$_2$)$_{20}$ and hexane), 4.1 (d, 6H, P(OCH$_3$)$_2$), 4.4 (t, 2H, CH$_2$O). Anal. Calcd. for C$_{25}$H$_{51}$O$_5$P.0.15C$_6$H$_{14}$: C, 65.40; H, 11.27; P, 6.52. Found: C, 65.39; H, 11.26; P, 6.74.

EXAMPLE 7

Preparation of dimethyl 3β-cholesten-5-ylcarbonylphosphonate (Formula VII: R=C$_{27}$H$_{46}$, R$^1$=R$^2$=CH$_3$)

A mixture of cholestenyl chloroformate (4.6 g, 10 mmol) and P(OMe)$_3$ (15 mL) was heated to 114° C. and maintained under reflux for 2 hours, allowed to cool to room temperature, and diluted with hexane (20 mL). The precipitate was filtered, washed with cold hexane, and recrystallized from hexane. Drying in vacuo yielded colorless plates (4.7 g, 90% yield); mp 176–177° C.; IR (KBr): υ 3400, 2940, 2910, 2840, 1705, 1460, 1370, 1325, 1280, 1240 cm$^{-1}$; $^1$H NMR (CDCl$_3$) δ0.30–2.70 (m, 44H, cholesteryl CH$_3$, CH$_2$, CH), 3.90 (d, 6H, P(OCH$_3$)$_2$), 4.60 (m, 1H, cholesteryl 3α-H), 5.35 (1H, cholesteryl CH=).

EXAMPLE 8

Preparation of Sodium Methyl 1-octadecyloxycarbonylphosphonate (Formula VII: R=CH$_3$(CH$_2$)$_{17}$—, R$^1$=CH$_3$, R$^2$=Na).

A mixture of NaI (553 mg, 3.69 mmol) and dimethyl 1-octadecyloxycarbonylphosphonate (1.0 g, 2.46 mmol) in a mixture of DMF (3 mL) and THF (10 mL) was stirred under argon in a flask protected from light. After 20 hours, a second portion of NaI (277 mg, 1.85 mmol) was added, and stirring was continued for a total of 44 hours, at which time TLC showed all the starting material to be gone. The solvents were removed on the rotary evaporator and the residue was triturated with acetone, filtered, and dried in vacuo over P$_2$O$_5$ to a white solid (0.96 g, 94% yield); mp 92–93° C.; IR (KBr): υ 2980, 2965, 2930, 2860, 1720–1690 br, 1470, 1270 cm$^{-1}$; $^1$H NMR (CDCl$_3$+CD$_3$OD) δ0.9–1.8 (m, 35H, CH$_3$(CH$_2$)$_{16}$), 3.7 (D, 3H, P(ONa)(OCH$_3$)), 4.2 (t, 2H, CH$_2$O). Anal. Calcd. for C$_{20}$H$_{40}$O$_5$NaP: C, 57.94; H, 9.75; Na, 5.55; P, 7.47. Found: C, 58.05; H, 9.66; N, 5.64; P, 7.63.

EXAMPLE 9

Preparation of Sodium Methyl 1-eicosanyloxycarbonylphosphonate (Formula VII: R=CH$_3$(CH$_2$)$_{19}$—, R$^1$=CH$_3$, R$^2$=Na)

Demethylation of dimethyl 1-eicosanyloxycarbonylphosphonate with NaI was carried out as described in Example 8 above except for the solvent, which was a mixture of DMF (3 mL), THF (8 mL), and acetone (2 mL); yield 0.86 g (84%); mp 95–96° C.; IR (KBr): υ 2960, 2930, 2860, 1735, 1470, 1235, 1220 cm$^{-1}$; $^1$H NMR (CDCl$_3$+CD$_2$OD) δ0.8–1.8 (m, 39H, CH$_3$(CH$_2$)$_{18}$), 3.8 (d, 3H, P(ONa)(OCH$_3$)), 4.2 (t, 2H, CH$_2$O). Anal. Calcd. for C$_{22}$H$_{44}$O$_5$NaP: C, 59.69; H, 10.04; N, 5.19; P, 7.00. Found: C, 59.94; H, 10.00; Na, 5.19; P, 7.06.

EXAMPLE 10

Preparation of Sodium Methyl 1-docosanyloxycarbonylphosphonate (Formula VII: R=CH$_3$(CH$_2$)$_{21}$—, R$^1$=CH$_3$, R$^2$=Na)

The title compound was prepared from dimethyl 1-docosanyloxycarbonyl phosphonate by demethylation using NaI as generally described in Example 8 above; 88% yield; mp 99–100° C.; IR (KBr): υ 2960, 2920, 2860, 1735, 1470, 1250 br cm$^{-1}$; $^1$H NMR (CDCl$_3$+CD$_3$OD) υ 0.8–1.8 (m, 43H, CH$_3$(CH$_2$)$_{20}$), 3.7 (d, 3H, P(ONa)(OMe)), 4.1 (t, 2H, CH$_2$O). Anal. Calcd. for C$_{24}$H$_{48}$O$_5$NaP: C, 61.24; H, 10.30; Na, 4.88; P, 6.58. Found: C, 61.61; H, 10.18; Na, 4.72; P, 6.33.

EXAMPLE 11

Preparation of Sodium Methyl 3β-cholesten-5-ylcarbonylphosphonate (Formula VII: R=C$_{27}$H$_{46}$, R$^1$=CH$_3$, R$^2$=Na)

Cholesteryl chloroformate (9.0 g, 20 mmol) was added slowly to refluxing P(OMe)$_3$ (30 mL), and refluxing was continued for 1 hour. The reaction mixture was then allowed to cool to room temperature, hexane (25 mL) was added, and the white solid was filtered, washed with hexane (2×25 mL), and dried in vacuo to obtain the triester dimethyl 3β-cholesten-5-ylcarbonylphosphonate (8.99 g, 86%); mp 171–176° C. A portion of dimethyl 3β-cholesten-5-ylcarbonylphosphonate (1.0 g, 1.0 mmol) was dissolved in a mixture of DMF (10 mL), THF (15 mL), and acetone (10 mL), and the solution was treated with NaI (431 mg, 2.88 mmol) with protection from light. After 24 hours of stirring under argon, the solvents were evaporated and the oily residue was triturated with acetone. Filtration and drying afforded a white solid (0.95 g, 94%); mp 275–276° C.; IR (KBr): υ 2950–2850, 1685 br, 1470, 1440, 1380, 1365, 1270, 1230 cm$^{-1}$; $^1$H NMR (CD$_3$OD) δ0.6–2.5 (m, 43H, cholestenyl CH$_3$, CH$_2$, CH); 3.7 (d, 3H, P(ONa)(OCH$_3$)), 4.5 (m, 2H, CH$_2$O), 5.4 (m, 1H, =CH). Anal. Calcd. for C$_{29}$H$_{48}$O$_5$NAP.0.2H$_2$O : C, 65.18; H, 9.15; Na, 4.30; P, 5.79. Found: C, 65.00; H, 9.14; Na, 4.24; P, 5.96.

EXAMPLE 12

Preparation of 1-octadecyloxycarbonylphosphonic acid (Formula VII: R=CH$_3$(CH2)$_{17}$—, R$^1$=R$^2$=H)

Me$_3$SiBr (0.812 mL, 6.15 mmol) was added to a solution of dimethyl octadecyloxycarbonylphosphonate (1.0 g, 2.46 mmol) in CH$_2$Cl$_2$ (20 mL) under argon, and the yellow solution was stirred at room temperature for 4 hours and evaporated under reduced pressure. Trituration of the oily residue with hexane, followed by filtration and drying afforded a hygroscopic white solid of the title compound (0.757 g, 81%); mp 81–82° C.; IR (KBr): υ 2960, 2920, 2860, 1730, 1720, 1475, 1465, 1265, 1240, 1225 cm$^{-1}$; $^1$H NMR (CDCl$_3$+CD$_3$OD) δ0.8–1.8 (m, 35H, CH$_3$ (CH$_2$)$_{16}$), 4.25 (t, 2H, OCH$_2$). Anal. Calcd. for C$_{19}$H$_{39}$O$_5$P.0.3H$_2$O : C, 59.43; H, 10.42; P, 8.07. Found: C, 59.77; H, 10.91; P, 8.21.

EXAMPLE 13

Preparation of 1-eicosanyloxycarbonylphosphonic acid (Formula VII: R=CH$_3$(CH$_2$)$_{19}$—, R$^1$=R$^2$=H)

By the general procedures of Example 12 and using dimethyl eiconsanyloxycarbonylphosphonate, the title compound was obtained in 77% yield; mp 87–89° C.; IR (KBr): υ 2960, 2930, 2860, 1735, 1470, 1235, 1220 cm$^{-1}$; $^1$H NMR (CDCl$_3$+CD$_3$OD) δ0.9–1.8 (m, 39H, CH$_3$ (CH$_2$)$_{18}$), 4.2 (t, 2H, OCH$_2$). Anal. Calcd. for C$_{21}$H$_{43}$O$_5$P: C, 62.03; H, 10.68; P, 7.62. Found: C, 62.41; H, 10.92; P, 7.36.

EXAMPLE 14

Preparation of 1-docosanyloxycarbonylphosphonic acid (Formula VII: R=CH$_3$(CH$_2$)$_{21}$—, R$^1$=R$^2$=H)

By the general procedures of Example 12 and using dimethyl docosanyloxycarbonylphosphonate, the title compound was obtained in 77% yield; mp 92–93° C.; IR (KBr): υ 2950, 2910, 1730, 1465, 1240–1210 cm$^{-1}$; $^1$H NMR (CDCl$_3$+CD$_3$OD) δ0.8–1.8 (m, 43H, CH$_3$ (CH$_2$)$_{20}$), 4.3 (t, 2H, OCH$_2$). Anal. Calcd. for C$_{23}$H$_{47}$O$_5$P: C, 63.55; H, 10.92; P, 7.12. Found: C, 63.97; H, 11.06; P, 6.98.

EXAMPLE 15

Preparation of 3β-cholest-5-enylcarbonylphosphonic acid (Formula VII: R=C$_{27}$H$_{46}$, R$^1$=R$^2$=H).

By the general procedures of Example 12 and using dimethyl cholestenylcarbonylphosphonate, the title compound was obtained in 78% yield; mp 152–153° C. dec; IR (KBr): υ 3400, 2980–2950, 2870, 1720, 1470, 1440, 1385, 1260, 1225 cm$^{-1}$; $^1$H NMR (CDCl$_3$) δ0.5–2.5 (m, 43H, cholesteryl protons), 4.8 (m, 1H, OCH$_2$), 5.4 (m, 1H, cholestenyl =CH). Anal. Calcd. for C$_{28}$H$_{47}$O$_5$P.H$_2$O: C, 65.58; H, 9.65; P, 6.04. Found: C, 65.68; H, 9.82; P, 6.04.

EXAMPLE 16

Preparation of disodium 1-octadecyloxycarbonylphosphonate (Formula VII: R=CH$_3$(CH$_2$)$_{17}$—, R$^1$=R$^2$=Na)

A stirred solution of 1-octadecyloxycarbonylphosphonic acid (100 mg, 0.264 mmol) in a mixture of MeOH (8 mL) and CHCl$_3$ (8 mL) was cooled to −5° C. under argon and to it was added dropwise over 5–10 minutes a solution of NaOMe in MeOH, prepared by dissolving Na metal (12.1 mg, 0.528 mmol) in anhydrous MeOH (8 mL). After 1.5 hours of stirring, the solvents were evaporated, fresh MeOH (10 mL) was added, and the mixture was kept in a sonication bath until a fine white solid formed. Filtration, extensive washing with MeOH to remove any mono- or dimethyl ester, and drying in vacuo over P$_2$O$_5$ afforded a white powder (70 mg, 63%); mp>350° C.; IR (KBr): υ 2960, 2920, 2925, 1690, 1470, 1380 cm$^{-1}$. Anal. Calcd. for C$_{19}$H$_{37}$Na$_2$O$_5$P.0.3CH$_3$OH: C, 53.64; H, 8.93; Na, 10.64; P, 7.17. Found: C, 53.50; H, 8.79; Na, 10.46; P, 7.07.

EXAMPLE 17

Preparation of disodium 1-eicosanyloxycarbonylphosphonate (Formula VII: R=CH$_3$(CH$_2$)$_{19}$—, R$^1$=R$^2$=Na)

By the general procedures of Example 16 and using 1-eicosanyloxycarbonyl phosphonic acid, the title compound was obtained in 81% yield; white powder, mp>350°; Anal. Calcd. for C$_{21}$H$_{41}$Na$_2$O$_5$P.0.3CH$_3$OH: C, 55.59; H, 9.26; Na, 9.99; P, 6.73. Found: C, 55.80; H, 9.24; Na, 9.78; P, 6.74.

EXAMPLE 18

Preparation of disodium docosanyloxycarbonylphosphonate (Formula VII: R=CH$_3$(CH$_2$)$_{21}$—, R$^1$=R$^2$=Na)

By the general procedures of Example 16 and using 1-docosanyloxycarbonyl phosphonic acid, the title compound was obtained in 98% yield; white powder, mp 270–272° C., prior softening; IR (KBr) υ 2980–2900, 2860, 1680, 1480, 1390 cm$^{-1}$. Anal. Calcd. for C$_{23}$H$_{45}$Na$_2$O$_5$P.1.3CH$_3$OH: C, 56.09; 9.74; Na, 8.84; P, 5.95. Found: C, 56.30; H, 9.75; Na, 8.68; P, 5.84.

EXAMPLE 19

Preparation of disodium cholesterylcarbonylphosphonate (Formula VII: R=C$_{27}$H$_{46}$, R$^1$=R$^2$=Na)

By the general procedures of Example 16 and using 3β-cholest-5-enylcarbonylphosphonic acid, the title compound was obtained in 68% yield; hygroscopic white powder, mp 295–300° C., softening above 230° C.; IR (KBr): υ 3410, 2940, 2900, 2860, 1670, 1470, 1440, 1380, 1365, 1330 cm$^{-1}$. Anal. Calcd. for C$_{28}$H$_{45}$O$_5$Na$_2$P.0.8CH$_3$OH.1.2H$_2$O : C, 59.03; H, 8.72; Na, 7.85; P, 5.29. Found: C, 58.90; H, 8.45; Na, 7.58; P, 5.28.

EXAMPLE 20

Preparation of 3'-azido-3'-deoxy-5'-O-(1-octadecyloxycarbonyloxyphosphinyl)thymidine (Formula II: R=$CH_3(CH_2)_{17}$—, m=0, Z=$NH_4$+, W=W'=O, N=3'-azido-3'-deoxythymidine)

Method A. $PCl_5$ (1.68 g, 8.10 mmol) was added to a solution of dimethyl 1-octadecyloxycarbonylphosphonate (3.1 g, 7.63 mmol) in dry $CCl_4$ (40 mL) and the reaction mixture was heated to reflux for 3 hours. The unreacted $PCl_5$ was decomposed by passing dry $SO_2$ gas through the solution at room temperature for 5 minutes, and the $CCl_4$, $SOCl_2$, and $POCl_3$ were distilled off under high vacuum (0.01–0.05 Torr) at 40° C. The residue was taken up in dry DMF (6 mL), taking extreme care to minimize exposure to moisture, and the solution was cooled to −50° C. in a dry ice-acetone bath. AZT was thoroughly dried by repeated addition and rotary evaporation of freshly redistilled pyridine, a sample of the anhydrous nucleoside (0.68 g, 2.55 mmol) was dissolved in dry DMF (1 mL), and the solution was pre-cooled to −50° C. and added at once under argon via a syringe to the stirred DMF solution of alkoxycarbonylphosphonyl chloride reagent. When addition was complete, the reaction mixture was allowed to come to room temperature and stirring was continued for 24 hours. The solvent was evaporated under reduced pressure, and the foamy residue was purified by flash chromatography on silica gel (98:2 $CHCl_3$—MeOH) to obtain the desired PFA-AZT triester (title compound, except Z=$CH_3$) as a colorless solid which was used directly in the next step; yield 1.1 g (22%).

Solid NaI (0.18 g, 1.2 mmol) was added to a solution of the PFA-AZT triester (0.55 g, 0.86 mmol) in dry THF (10 mL) in flask wrapped in aluminum foil, and stirring was continued under argon at room temperature for 24 hours. After evaporation of the solvent under reduced pressure, the residue was applied onto a DEAE-cellulose column ($HCO_3^{-1}$ form). The column was eluted successively with distilled $H_2O$ and 0.05 M $NH_4HCO_{3-}$. Fractions of the latter eluent containing the desired product were pooled and freeze-dried to a colorless solid (220 mg, 40% yield); mp 224° C. dec; TLC: $R_f$ 0.25 (silica gel, 85:15:1 $CHCl_3$—MeOH-28% $NH_4OH$); HPLC: 4.4 minutes ($C_{18}$ silica gel, 30% MeCN in 0.01 M $NH_4OAc$, pH 6.7; 1 mL/minute); IR (KBr): υ 3400, 3150 br, 2890, 2820, 2080 ($N_3$), 1710–1650 br, 1455, 1390, 1240 $cm^{-1}$; $^1H$ NMR ($d_4$-DMSO, 500 MHz) δ0.40–2.80 (m, 40H, $CH_3(CH_2)_{16}$, 5-Me, $C_2$,—H), 4.0–4.5 (m, 6H, $CH_2O$, $C_3$,—H, $C_4$,—H, $C_5$,—H), 6.15 (t, 1H, $C_1$,—H), 7.80 (s, 1H, $C_6$—H). Anal. Calcd. for $C_{29}H_{50}N_5O_8P.NH_3.0.5H_2O$: C, 53.28; H, 8.33; P, 4.74. Found: C, 53.40; H, 8.49; P, 4.75.

Method B. A mixture of 1-octadecyloxycarbonylphosphonic acid (0.15 g, 0.4 mmol) and AZT (0.216 g, 0.81 mmol) was rigorously dried by repeated addition and rotary evaporation of freshly distilled pyridine (3×10 mL). The dried reactants were redissolved in pyridine (5 mL) and the solution was flushed with a current of argon for 15 minutes at room temperature. $Cl_3CCN$ (0.54 g, 4.0 mmol) was then added and the reaction mixture kept at 50–60° C. in an oil bath overnight under argon. The solvent was removed by rotary evaporation and the residue redissolved in $CH_2Cl_2$ (40 mL). The organic layer was washed with $H_2O$ (2×20 mL), dried over $Na_2SO_4$, and evaporated. Flash chromatography on silica gel with $CHCl_3$—MeOH-28% $NH_4OH$ (85:15:1) as the eluent yielded a white solid (85 mg, 34%; mp 220° C. IR and $^1H$ NMR spectra of this material and of the product obtained by Method A above were virtually indistinguishable.

EXAMPLE 21

Preparation of 3'-Azido-3'-deoxy-5'-O-(1-eicosanyloxycarbonyloxy phosphinyl)thymidine (Formula II: R=$CH_3(CH_2)_{19}$—, m=0, Z=$NH_4$+, W=W'=O, N=3'-azido-3'-deoxythymidine)

Method A. Treatment of dimethyl 1-eicosanyloxycarbonylphosphonate (1.66 g, 3.82 mmol) with $PCl_5$ (0.84 g, 4.04 mmol) in $CCl_4$ (20 mL) as described in Example 20, Method A above, followed by reaction with AZT (0.68 g, 2.55 mmol) and purification by silica gel flash chromatography (98:2 $CHCl_3$—MeOH) afforded the desired AZT-PFA triester (title compound, except X=$CH_3$) as a waxy white solid (0.76 g, 30% yield). Further reaction of that triester (0.50 g, 0.75 mmol) directly with NaI (0.16 g, 1.1 mmol) in THF (80 mL) under argon in the absence of light, followed by purification on DEAE-cellulose ($HCO_3$—form; $H_2O$, then 0.05 M $NH_4HCO_3$) afforded the title compound as a colorless solid (165 mg, 33%); mp 230° C. dec; TLC: $R_f$ 0.29 (silica gel, 85:15:1 $CHCl_3$—MeOH-28% $NH_4OH$); HPLC: 4.7 minutes ($C_{18}$ silica gel, 30% MeCN in 0.01 M $NH_4OAc$, pH 6.7; 1.0 mL/minute); IR (KBr): υ3450, 3250 sh, 2920, 2850, 2100 ($N_3$), 1710–1640 br, 1470, 1400, 1370, 1250 $cm^{-1}$; $^1H$ NMR ($d_6$-DMSO, 500 MHz) δ0.60–2.60 (m, 44H, $CH_3(CH_2)_{18}$), 5-Me, $C_2$,—H), 4.0–4.6 (m, 6H, $CH_2O$, $C_3$,—H, $C_4$,—H, $C_5$,—H,), 6.15 (t, 1H, $C_1$,—H), 7.80 (s, 1H, 6-H). Anal. Calcd. for $C_{31}H_{54}N_5O_8P.NH_3.0.5H_2O$: C, 54.61; H, 8.57; P, 4.54. Found: C, 54.57; H, 8.40; P, 4.68.

Method B. Coupling of 1-eicosanyloxycarbonylphosphonic acid (0.42 g, 1.02 mmol) and AZT (0.55 g, 2.05 mmol) by the $CCl_3CN$ method as described in Example 20, Method B above, followed by flash chromatography on silica gel (85:15:1 $CHCl_3$—MeOH-28% $NH_4OH$), gave a white solid (133 mg, 49%); mp 228° C. dec. IR and $^1H$ NMR spectra of this material and of the product obtained from Method A via the $PCl_5$ method were virtually indistinguishable.

EXAMPLE 22

3'-Azido-3'-deoxy-5'-O-(1-docosanyloxycarbonyloxyphosphinyl) thymidine (Formula II: R=$CH_3(CH_2)_{21}$—, m=0, Z=$NH_4$+, W=W'=O, N=3'-azido-3-deoxythymidine)

Method A. Treatment of dimethyl 1-docosanyloxycarbonylphosphonate (1.75 g, 3.82 mmol) with $PCl_5$ (0.84 g, 4.04 mmol) in $CCl_4$ (20 mL) as described in Example 20, Method A above, followed by reaction with AZT (0.77 g, 2.90 mmol) and purification by silica gel flash chromatography (98:2 $CHCl_3$—MeOH) afforded the AZT-PFA triester (title compound, except X=$CH_3$) as a waxy white solid (1.0 g, 50% yield). Further reaction of the triester (0.50 g. 0.75 mmol) directly with NaI (0.16 g, 1.1 mmol) in THF (8 mL) under argon, followed by purification on DEAE-cellulose ($HCO_3$-form; $H_2O$, then 0.05 M $NH_4HCO_3$) afforded the title compound as a colorless solid (140 mg, 28%); mp 238° C. dec; TLC: Rf0.31 (silica gel, 85:15:1 $CHCl_3MeOH$-28% $NH_4OH$); HPLC: 4.8 minutes ($C_{18}$ silica gel, 30% MeCN in 0.01 M $NH_4OAc$, pH 6.7; 1.9 mL/minute); IR (KBr): υ 3449, 3200, 2920, 2850, 2100 ($N_3$), 1710–1680 br, 1470, 1400, 1320, 1250 $cm^{-1}$; $^1H$ NMR ($d_6$-DMSO, 500 MHz) δ 0.65–2.60 (m, 48H, $CH_3(CH_2)_{20}$), 5-Me, $C_2$; —H, 4.0–4.5 (m, 6H, $CH_2O$, $C_3$'—H, $C_4$; —H), 6.15 (t, 1H, $C_1$,—H), 7.83 (s, 1H, 6-H). Anal. Calcd. for $C_{33}H_{58}N_5O_8P\cdot NH_3\cdot 1.25H_2O$: C, 54.79; H, 8.85; P. 4.28. Found: C, 54.64; H, 8.56; P. 4.11.

Method B. Coupling of 1-docosanyloxycarbonylphosphonic acid (0.25 g, 0.58 mmol) and AZT (0.0.31 g, 1.16 mmol) by the $CCl_3CN$ method as described above in Example 20 Method B, followed by flash chromatography on silica gel (85:15:1 $CHCl_3$—MeOH-28%$NH_4OH$), gave the title compound as a white solid (120 mg, 30%); mp 230° C. dec. IR and $^1$NMR spectra of this material and of the product obtained from Method A via the $PCl_5$ method were closely superimposable.

EXAMPLE 23

Preparation of 3'-Azido-3'-deoxy-5'-O-[3β-cholest-5-enyl]oxycarbonyloxyphosphinyl]thymidine (Formula II: $R=C_{27}H_{46}$—, m=0, W=W'=O, Z=$NH_4^+$, N=3'-azido-3'-deoxythymidine)

Treatment of dimethyl 3β-cholesten-5-ylcarbonylphosphonate (4.0 g, 7.65 mmol) with $PCl_5$ (1.60 g, 7.65 mmol) in $CCl_4$ (40 mL) as described in Example 20 Method A, followed by reaction with AZT (0.68 g, 2.55 mmol) (dimethyl cholesterylcarbonylphosphonate: AZT molar ratio=3.0) and purification by silica gel flash chromatography (98:2 $CHCl_3$—MeOH) afforded the triester (title compound, except X=$CH_3$) as a colorless solid (1.18 g, 61% yield); mp 102° C. (lit. mp 100° C.); TLC: $R_f$ 0.58 (silica gel, 98:2 $CH_2CL_2$—MeOH). Further reaction of that triester (2.42 g, 0.75 mmol) (combined from two runs) with NaI (0.51 g, 3.42 mmol) in THF (14 mL) under argon, followed by purification on DEAE-cellulose ($HCO_3^-$ form; $H_2O$, then 0.05 M $NH_4HCO_3$) afforded the title compound as a colorless solid (1.68 g, 67%); mp 220° C. dec; TLC: $R_f$ 0.23 (silica gel, 85:15:1 $CHCl_3^-$ MeOH-28% $NH_4OH$); HPLC: 4.2 minutes ($C_{18}$ silica gel, 30% MeCN in 0.01 M $NH_4OAc$, pH 6.7; 1.0 mL/minute), with no detectable AZT; IR (KBr): υ 3420, 3160, 2940, 2105 ($N_3$), 1710–1670 br, 1470, 1440, 1400, 1385, 1325, 1250 cm$^{-1}$; $^1$H NMR ($d_6$-DMSO, 500 MHz) δ0.4–2.6 (m, 49H, cholestenyl $CH_3$, $CH_2$, CH, 5-Me, $C_2$,—H), 4.0–4.5 (m, 6H, cholestenyl 3β-H, $C_3$,—H, $C_4$,—H, $C_5$,—H), 5.25 (m, 1H, cholestenyl CH=), 6.15 (t, 1H, $C_1$—H), 7.80 (s, 1H, 6-H). Anal. Calcd. for $C_{38}H_{57}N_5O_8PNH_3\cdot H_2O$: C, 58.60; H, 8.15; N, 10.79; P; 3.98. Found: C, 58.90; H, 8.05; N, 10,44; P; 3.75.

EXAMPLE 24

Preparation of di-O-(3'-azido-3'-deoxythimidin-5'-yl) (3β-cholest-5-enyl)oxycarbonylphosphonate (Formula III: $R=C_{27}H_{46}$—, m=0, W=W'=O, N=N'=3'-azido-3'-deoxythymidine)

A mixture of dimethyl 3β-cholesten-5-ylcarbonylphosphonate (4.0 g, 7.65 mmol) and $PCl_5$ (1.62 g, 7.65 mmol in dry $CCl_4$ (40 mL) was refluxed for 48 hours and evaporated dryness under reduced pressure. The residue was taken up in dry DMF (10 mL), the solution cooled to −50° C. in a dry ice-acetone bath, a pre-cooled (−50° C.) solution of AZT (1.36 g, 5.1 mmol) (dimethyl cholestenyl-carbonyl phosphonate:AZT molar ratio=1.5) in dry DMF (1 mL) added under argon via a syringe, and the mixture stirred at room temperature for 48 hours. Solvent evaporation under high vacuum, followed by flash chromatography (silica gel, 97:3 $CHCl_3$—MeOH, gave colorless crystals of the title compound (0.35 g, 14%); mp 123–124° C.; TLC: $R_f$ 0.60 (85:15:1 $CHCl_3$—MeOH-28% $NH_4OH$); IR (KBr): υ 3450, 3190, 3050, 2950, 2860, 2100 ($N_3$), 1750–1650 br, 1470, 1400, 1385, 1365, 1320, 1275, 1225 cm$^{-1}$; $^1$H NMR ($d_6$DMSO, 500 MHz) δ0.6–2.6 (m, 54H, cholestenyl $CH_3$, $CH_2$, CH, 5-Me, $C_2$,—H), 4.00–4.55 (m, 5H, cholestenyl 3α-H, $C_3$,—H, $C_4$,—H, $C_5$,—H), 5.20 m, 1H, cholestenyl CH=), 6.1 (t, 2H, $C_1$,—H), 7.45 (s, 2H, 6—H). Anal. Calcd. for $C_{48}H_{69}N_{10}O_{11}P_3H_2O$: C, 55.06; H, 7.12; N, 13.37; P, 2.96. Found: C, 54.85; H, 6.74; N, 13.06; P, 2.66.

EXAMPLE 25

Preparation of 3'-azido-3'-deoxy-5'-O-[(hexadecyloxypropoxy) (hydroxy)phosphono (carbonyl]thymidine (Formula IV: $R=CH_3(CH_2)_{15}O(CH_2)_3$—, Z=hydrogen, m=0, W=W'=O, N=3'-azido-3'-deoxythymidine)

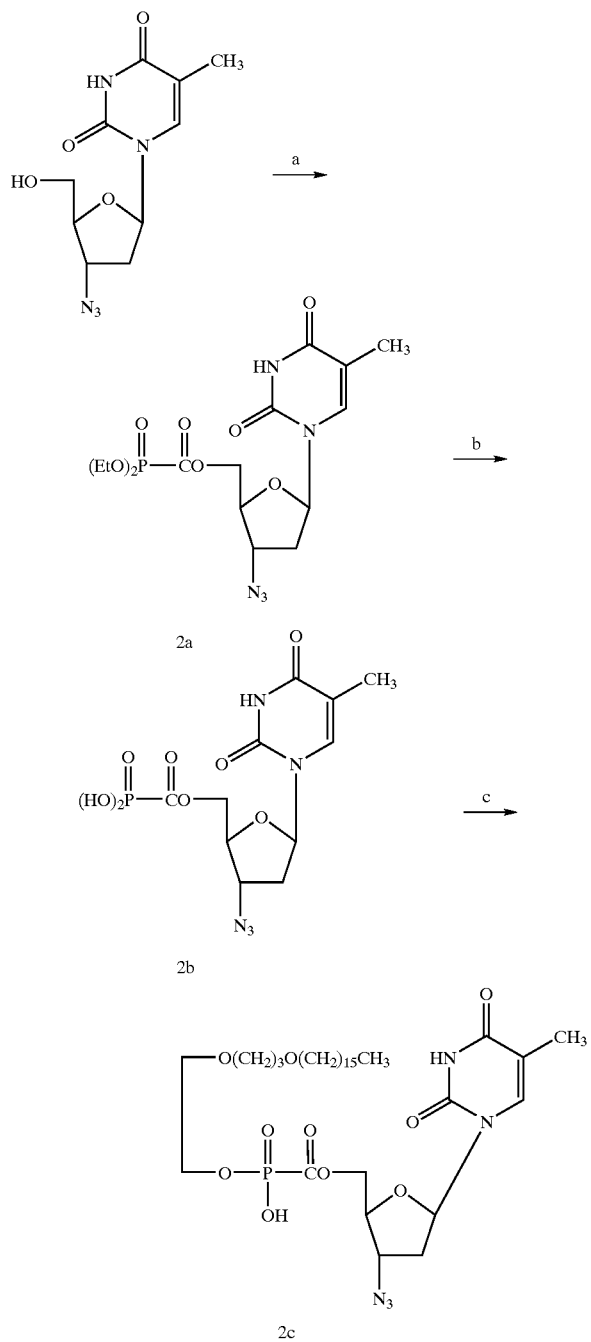

-continued

Reagents: (a) (EtO)₂P(O)C(O)Cl, DMAP, pyridine;
(b) bromotrimethylsilane, CH₃CN;
(c) 3-hexadecyloxy-1-propanol, DCC, pyridine.

Part A. 3'-azido-3'-deoxy-5'-O-[(diethoxyphosphono) carbonyl]thymidine (2a in Above Scheme)

To a stirred solution of diethylphosphonoformic chloride (1.0 g, 5 mmol) in dry pyridine (35 mL) was added a solution of AZT (1.0 g, 3.75 mmol) and dimethylaminopyridine (0.25 g, 2 mmol). The mixture was stirred overnight. The mixture was filtered and the filtrate concentrated in vacuo. The residue was purified by flash column chromatography to yield 2a (1.29 g, 80%) as a foamy white solid.

Part B. 3'-azido-3'-deoxy-5'-O-[(dihydroxyphosphono) carbonyl]thymidine (2b in above scheme)

To a solution of diethyl phosphonate 2a (4.2 g, 9.7 mmol) in dry acetonitrile (30 mL) was added bromotrimethylsilane (10 g, 65 mmol) and the mixture was stirred one hour at room temperature. To the reaction mixture was added methanol (10 mL) and pyridine (5 mL) and the mixture was concentrated in vacuo to give the phosphonate 2b as a foamy solid which was used in the next step without further purification.

Part C. 3'-azido-3'-deoxy-5'-)-[(hexadecyloxypropy) (hydroxy) phosphono(carbonyl]thymidine (2c in above scheme)

To a solution of the free phosphate 2b (0.5 g, 1.3 mmol) in pyridine (30 mL) was added 3-hexadecyloxy-1-propanol (0.75 g, 2.3 mmol) and the solution was cooled in an ice bath. A solution of dicyclohexyldiimide (1.0 g, 5 mmol) in dichloromethane (7 mL) was added dropwise with stirring and the mixture was left at room temperature overnight. The reaction mixture was filtered and the filtrate was concentrated in vacuo and the residue was purified by flash chromatography over silica gel using 80:20 (by vol.) CH₂Cl₂/MeOH to elute the coupled product 2c (540 mg, 63%).

EXAMPLE 26

Preparation of Sodium 3'-Azido-3'-deoxy-5'-O-(hexadecyloxypropoxy) carbonyloxyphosphinyl) thymidine (Formula V: R=CH₃(CH₂)₁₅O(CH₂)₃—, N=3'-azido-3'-deoxythymidine, m=0, W=W'=O, Z=Na⁺)

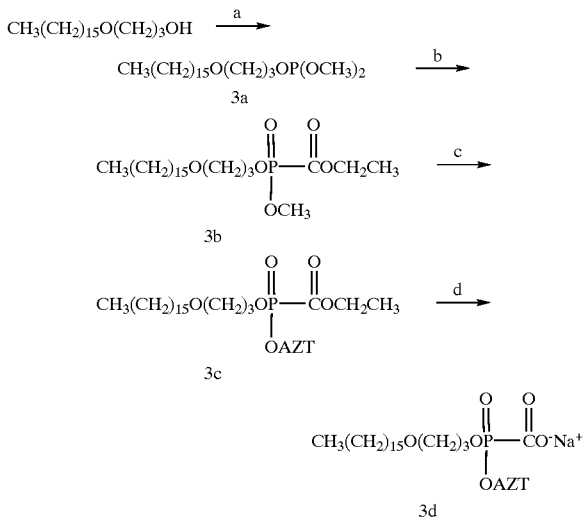

-continued

Reagents: (a) (MeO)₂PCl, Et₃N;
(b) ethyl chloroformate;
(c) 1. PCl₅, CCl₄; 2. AZT, DMF;
(d) 0.1 N NaOH, EtOH Part A. (Hexadecyloxypropoxy)dimethoxyphosphite (3a in Above Scheme)

To a stirred solution of dimethylphosphorochloridite (0.9 g, 7 mmol) in dry CH₂Cl₂ (30 mL) cooled to −20° C. was added dropwise a CH₂Cl₂ solution of 3-hexadecyloxy-1-propanol (2.1 g, 7 mmol) and triethylamine (0.9 g, 0.9 mmol) over 30 minutes. The mixture was allowed to warm to room temperature over 2 hours, then vacuum filtered to remove triethylamine hydrochloride. The filtrate was concentrated in vacuo and the residue purified by flash chromatography over silica gel using 9:1 (by vol.) hexane/ethyl acetate as the eluting solvent. Evaporation of the pure fractions yielded 1.96 g of 3a as a colorless oil (70%).

Part B. (Hexadecyloxypropoxy)(methoxy) ethyloxycarbonylphosphonate (3b in Above Scheme)

A mixture of 3a (1.96 g, 5 mmol) and ethyl chloroformate (10 mL) was stirred for 5 hours at room temperature. The ethyl chloroformate was evaporated in vacuo and the residue was purified by flash column chromatography over silica gel using 9:1 hexane:ethyl acetate to elute 1.8 g of 3b as a colorless oil (80%).

Part C. Sodium 3'-azido-3'-deoxy-5'-O-(hexadecyloxypropoxy) (carbonyloxyphosphinyl)thymidine (3d in above scheme)

PCl₅ (0.9 g, 4.2 mmol) was added to a solution of 3b (1.8 g, 4 mmol) in dry CCl₄ (15 mL) and the reaction mixture was heated to reflux for 3 hours. The unreacted PCl₅ was decomposed by passing dry SO₂ gas through the solution at room temperature for 5 minutes and the CCl₄, SOCl₂, and POCl₃ were distilled off under high vacuum (40° C., 0.01–0.05 Torr). The residue was taken up in dry DMF (20 mL), and the solution was cooled to −50° C. in a dry ice-acetone bath. AZT (anhydrous, 1.07 g, 4 mmol) was dissolved in dry DMF (5 mL), and the solution was added all at once to the stirred DMF solution of the phosphonyl chloride reagent. When addition was complete, the reaction mixture was allowed to warm to room temperature and stirring was continued for 24 hours. The solvent was evaporated under reduced pressure, and the residue was purified by flash chromatography on silica gel (95:5 CHCl₃/MeOH) to obtain 0.56 g of PFA-AZT triester 3c as a colorless solid (yield 20%).

Aqueous sodium hydroxide (0.1 N, 0.5 mL) was added to a stirred suspension of the PFA-AZT triester 3c (560 mg) in ethanol (0.5 mL) and stirred for 1 hour at room temperature. The solid was collected by vacuum filtration, rinsed thoroughly with cold ethanol and recrystallized from ethanol to give 550 mg (90%) 3d as a white solid.

EXAMPLE 27

HIV Proliferation Assay

Compounds of the invention were tested in a plaque-forming assay of HIV-1 proliferation in a human CD4+ lymphocytic cell line (HT-4) by the procedures described in K. Y. Hostetler et al., *J. Biol. Chem.*, 265:6112–6117 (1990); and K. Y. Hostetler et al., *J. Biol. Chem.*, 266:11714–11717 (1991). Sodium methyl 1-octadecylcarbonylphosphonate and sodium methyl 1-eicosanylcarbonylphosphonate were found to reduce the number of viral plaques by 35% when used at a concentration of 1 μM, the highest concentration achievable in the growth medium with these very hydrophobic compounds. By comparison, Foscarnet had an IC₅₀ of 133 μM, suggesting that the monosodium salt of the long-chain diester derivatives might be taken up very efficiently in comparison with the trisodium salt Foscarnet. However, the concentration of both sodium methyl 1-octadecylcarbonylphosphonate and sodium methyl 1-eicosanylcarbonylphosphonate that was toxic to approximately 50% of the HT4-6C host ($TC_{50}$) was 10 μM ($TC_{50}$ is mean ±standard deviation and determined according to a visual standardized grading scale of cellular morphology after 3 days of drug treatment and as further specified in Example 27 below). Thus the selectivity index (SI), defined as the $TC_{50}$(HIV-1)/$EC_{50}$, was <10. ($EC_{50}$ is concentration to reduce HIV plaques by 50% and expressed as mean ±standard deviation). The $EC_{50}$(HIV-1) of the eicosanyl PFA-AZT conjugate, 3'-Azido-3'-deoxy-5'-O-(1-eicosanyloxycarbonyloxyphosphinyl) thymidine, was 0.05 μM versus 0.007 μM for AZT. Thus that eicosanyl PFA-AZT conjugate was 7-fold less active than AZT, but was 2,800 times more active than PFA. The cytotoxicity of 3'-azido-3'-deoxy-5'-O-(1-eicosanyloxycarbonyloxy phosphinyl) thymidine was slight to moderate at 0.1–1.0 μM, and significant at 10 and 100 μM; thus, its therapeutic selectivity (ca. 200) was also less than that of AZT. The cholestenyl PFA-AZT conjugate, 3'-Azido-3'-deoxy-5'-O-[3β-cholest-5-enyl]oxycarbonylphosphinyl) thymidine, had an $IC_{50}$ (HIV-1) of 0.25 μM and showed cytotoxicity comparable to 1-eicosanyloxycarbonylphosphonic acid at 10 and 100 μM. Thus, replacement of the eicosanyl group by a cholesterol moiety did not afford an advantage in terms of either antiviral potency or selectivity.

EXAMPLE 28

Activity Against AZT-resistant and PFA-resistant HIV Strains

Selected compounds of the invention, PFA (Foscarnet) and AZT were tested for activity against three HIV infected cell lines: 1) LAI E89K, a PFA-resistant HIV cell line this strain also has been referred to as 89LAI-Lys; see G. Tachedijian et al., *Virology*, 70:7171–7181 (1996)); 2) A018-post, an AZT-resistant HIV cell line; and 3) LA1, a wild-type HIV-1 cell line (not resistant). The assays were conducted by procedures of Example 27 above and as disclosed in K. Y. Hostetler et al., *J. Biol. Chem.*, 265:6112–6117 (1990); and K. Y. Hostetler et al., *J. Biol. Chem.*, 266:11714–11717 (1991). Results are set forth in Table 1 below, with $EC_{50}$, μM values (concentration of drug effective in reducing HIV plaques by 50%) set forth in the Table grid. For compounds of Examples 20–22, values reported are mean ±standard deviation, and are the averages of 3 separate experiments on different days, except for the values of AZT against A018 which data is from B. A. Larder et al., *Science*, 243:1731–1734 (1989); and B. A. Larder et al., *Science*, 246:1155–1158 (1989). For the compound of Example 25, values of tests conducted are set forth in the table.

EXAMPLE 29

Selectivity of compounds of the invention in HT4-6C cells

Selected compounds of the invention and PFA were tested for activity in HT4-6C cell by procedures disclosed in B. A. Larder et al., *Science*, 243:1731–1734 (1989). Results are set forth in Table 2 below, with $TC_{50}$, μM values (50% toxic concentration), and selectivity index ($TC_{50}$/$EC_{50}$) are set forth in the Table grid. The $TC_{50}$ values were determined using the following visual grading scale after 3 days to exposure to the tested drug compound: 4—normal appearance; 3—slight reduction of normal cells; 2–50% of cells appear normal; 1—sparse number of normal appearing cells; 0—no living cells. Values reported in the Table below are mean ±standard deviation.

TABLE 2

| Compound of Example # | $TC_{50}$ (μM) | Selectivity Index |
|---|---|---|
| 20 | 10 | 100 |
| 21 | 32 | 228 |
| 22 | 320 | 1000 |

EXAMPLE 30

Activity of compounds of the invention in CEM cells $TC_{50}$ values were also assessed by exposing rapidly dividing human T-Lymphoblastic Leukemia Cells (CEM cells) to selected compounds of the invention and PFA. Viable cell numbers were determined by propidium iodide staining and fluorescent flow cytometry according to procedures disclosed in Dangl et al., *Cytometry*, 2:395–401 (1982). Results are set forth in Table 3 below.

TABLE 3

| Compound of Example # | $TC_{50}$ (μM) | Selectivity Index |
|---|---|---|
| 20 | 28 | 280 |
| 21 | 36 | 257 |
| 22 | 93 | 291 |
| 25 | 65 | 382 |

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A compound selected from the group consisting of:
 3'-azido-3'-deoxy-5'-O-(1-octadecyloxycarbonylphosphinyl)thymidine;

TABLE 1

| Virus | PFA | AZT | Compound of Example 20 | Compound of Example 21 | Compound of Example 22 | Compound of Example 25 |
|---|---|---|---|---|---|---|
| HIV-1$_{LAI}$ | 133 ± 54 | 0.013 ± 0.006 | 0.10 ± 0.15 | 0.14 ± 0.16 | 0.32 ± 0.20 | 0.17; <0.01 |
| LAI-E89K | >1000 | 0.009 ± 0.005 | 0.13 ± 0.14 | 0.009 ± 0.007 | 0.17 ± 0.11 | 1.3 |
| A018-post | 65 ± 13 | 4.0, 2.3 | 0.30 ± 0.32 | 0.53 ± 0.68 | 0.77 ± 1.1 | 13; 2.7 |

3'-azido-3'-deoxy-5'-O-(1-eicosanyloxycarbonylphosphinyl)thymidine;

3'-azido-3'-deoxy-5'-O-(1-docosanyloxycarbonylphosphinyl)thymidine; and

3'-azido-3'-deoxy-5'-O-[(3β-cholest-5-enyl)oxycarbonylphosphinyl)]thymidine.

2. A compound of claim 1 wherein the compound is 3'-azido-3'-deoxy-5'-O-(1-octadecyloxycarbonylphosphinyl)thymidine.

3. A compound of claim 1 wherein the compound is 3'-azido-3'-deoxy-5'-O-(1-eicosanyloxycarbonylphosphinyl)thymidine.

4. A compound of claim 1 wherein the compound is 3'-azido-3'-deoxy-5'-O-(1-docosanyloxycarbonylphosphinyl)thymidine.

5. A compound of claim 1 wherein the compound is 3'-azido-3'-deoxy-5'-O-[(3βcholest-5-enyl)oxycarbonylphosphinyl)]thymidine;

6. A method of treating mammalian cells infected with an HIV virus comprising administering to the cells an effective anti-HIV amount of a compound of any one of claims 2 through 5.

7. The method of claim 6 wherein the HIV virus infecting the cells is resistant to a reverse transcriptase inhibitor.

8. A method of treating a mammal suffering from an HIV infection comprising administering to the mammal a therapeutically effective amount of a compound of any one of claims 2 through 5.

9. A pharmaceutically composition comprising a pharmaceutically acceptable carrier and a therapeutically effective amount of a compound of any one of claims 2 through 5.

10. A compound of the formula IIA:

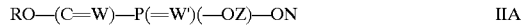

RO—(C=W)—P(=W')(—OZ)—ON            IIA wherein R is alkyl having from 8 to 30 carbon atoms;

W and W' are each O;

N is 5'-{3',5'-dideoxy-3'-azidothymidinyl}; and

Z is hydrogen or a pharmaceutically acceptable cation.

* * * * *